(12) United States Patent
Peh et al.

(10) Patent No.: US 10,835,663 B2
(45) Date of Patent: Nov. 17, 2020

(54) SUBCUTANEOUS IMPLANTABLE DEVICE FOR GUIDING A VASCULAR ACCESS MEMBER AND METHOD FOR VASCULAR ACCESS

(71) Applicants: Agency for Science, Technology and Research, Singapore (SG); Singapore Health Services Pte Ltd, Singapore (SG)

(72) Inventors: Ruey Feng Peh, Singapore (SG); Soo Ghim Lim, Singapore (SG); Yee Han Kuan, Singapore (SG); Yanling Toh, Singapore (SG); Hsien Ts'ung Tay, Singapore (SG); Seck Guan Tan, Singapore (SG)

(73) Assignees: Agency for Science, Technology and Research, Singapore (SG); Singapore Health Services Pte Ltd, Singapore (SG)

( * ) Notice: Subject to any disclaimer, the term of this patent is extended or adjusted under 35 U.S.C. 154(b) by 184 days.

(21) Appl. No.: 15/542,314

(22) PCT Filed: Jan. 7, 2016

(86) PCT No.: PCT/SG2016/050007
§ 371 (c)(1),
(2) Date: Jul. 7, 2017

(87) PCT Pub. No.: WO2016/111650
PCT Pub. Date: Jul. 14, 2016

(65) Prior Publication Data
US 2018/0272056 A1    Sep. 27, 2018

(30) Foreign Application Priority Data
Jan. 8, 2015  (SG) ............ 10201500141Q

(51) Int. Cl.
*A61M 1/36* (2006.01)
*A61M 39/02* (2006.01)

(52) U.S. Cl.
CPC ........ *A61M 1/3655* (2013.01); *A61M 1/3653* (2013.01); *A61M 1/3661* (2014.02);
(Continued)

(58) Field of Classification Search
CPC .............. A61M 1/3655; A61M 1/3653; A61M 1/3661; A61M 39/0208; A61M 39/0247;
(Continued)

(56) References Cited

U.S. PATENT DOCUMENTS 4,025,964 A * 5/1977 Owens ............... A61M 39/0247
                                                    623/11.11
4,413,924 A * 11/1983 Ijima ........................ E02B 3/06
                                                     405/31
(Continued)

FOREIGN PATENT DOCUMENTS

JP     2003530914    10/2003
JP     2005342508    12/2005
(Continued)

OTHER PUBLICATIONS

Extended European Sear Report dated Sep. 3, 2018 from European Application No. 16735240.0.
(Continued)

*Primary Examiner* — Nathan R Price
*Assistant Examiner* — Mark A Igel
(74) *Attorney, Agent, or Firm* — Crockett & Crockett, PC; K. David Crockett, Esq.; Niky Economy Syrengelas, Esq.

(57) ABSTRACT

A subcutaneous implantable device for guiding a vascular access member, the device including a channel defined by a
(Continued)

through-hole in the device, wherein the channel is configured to guide the vascular access member there-through to a vascular site; and anchoring means adapted for fixedly attaching, in a form of using suture, tissue ingrowth, tissue encapsulation or tissue adhesion, the device to at least one of a dermis or a subcutaneous tissue at a position underneath the dermis to allow repeated access of the vascular access member through the channel to the vascular site, wherein the device is dimensioned to allow the device to be attached through the anchoring means for anchoring the entire device at a distance away from the vascular site, A method of creating scar tissue track for vascular access is also disclosed where the subcutaneous implantable device for guiding vascular access member is first implanted sub-dermally, the dermis is palpated to feel for the device location and orientation, the guiding channel is accessed using the sharp vascular access member and following the angle of the guiding channel to access the vascular site and repeating the steps till scarred tissue track is created and finally, switching the sharp vascular access member to a blunt vascular access member to access the vascular site via the scarred tissue track.

18 Claims, 15 Drawing Sheets

(52) U.S. Cl.
CPC ..... *A61M 39/0208* (2013.01); *A61M 39/0247* (2013.01); *A61M 2039/0223* (2013.01); *A61M 2039/0238* (2013.01); *A61M 2039/0258* (2013.01); *A61M 2039/0261* (2013.01); *A61M 2039/0291* (2013.01); *A61M 2205/582* (2013.01)

(58) Field of Classification Search
CPC .. A61M 2039/0233; A61M 2039/0238; A61M 2039/0258; A61M 2039/0261; A61M 2039/0291; A61M 2205/582
See application file for complete search history.

(56) References Cited

U.S. PATENT DOCUMENTS

| | | | | |
|---|---|---|---|---|
| 4,569,675 A * | 2/1986 | Prosl | ............... | A61M 39/0208 128/DIG. 26 |
| 4,673,394 A * | 6/1987 | Fenton, Jr. | ....... | A61M 5/14276 128/912 |
| 4,781,695 A * | 11/1988 | Dalton | ............. | A61M 39/0208 604/175 |
| 4,886,501 A * | 12/1989 | Johnston | .......... | A61M 39/0208 604/175 |
| 5,013,298 A * | 5/1991 | Moden | ............. | A61M 39/0208 604/175 |
| 5,098,397 A * | 3/1992 | Svensson | ......... | A61M 39/0247 604/175 |
| 5,213,567 A * | 5/1993 | Masaki | ............... | A61M 1/008 604/175 |
| 5,263,930 A * | 11/1993 | Ensminger | ....... | A61M 39/0208 604/175 |
| 5,281,199 A * | 1/1994 | Ensminger | ....... | A61M 39/0208 604/288.03 |
| 5,350,360 A * | 9/1994 | Ensminger | ............. | A61M 5/00 604/288.03 |
| 5,356,381 A * | 10/1994 | Ensminger | ....... | A61M 39/0208 604/181 |
| 5,423,334 A * | 6/1995 | Jordan | ............... | G06K 7/0008 128/899 |
| 5,569,207 A * | 10/1996 | Gisselberg | ........... | A61M 25/02 604/175 |
| 5,810,789 A * | 9/1998 | Powers | ............ | A61M 25/0023 604/247 |
| 5,848,989 A * | 12/1998 | Villani | ............. | A61M 39/0208 604/288.02 |
| 6,017,355 A * | 1/2000 | Hessel | ............. | A61M 39/0247 606/184 |
| 6,960,185 B2 * | 11/2005 | Adaniya | .......... | A61M 39/0208 604/93.01 |
| 7,223,257 B2 * | 5/2007 | Shubayev | ........ | A61M 39/0247 604/175 |
| D546,440 S * | 7/2007 | Burnside | ...................... | D24/108 |
| D556,153 S * | 11/2007 | Burnside | ...................... | D13/167 |
| D574,950 S * | 8/2008 | Zawacki | ....................... | D24/108 |
| D578,203 S * | 10/2008 | Bizup | ........................... | D24/108 |
| D595,892 S * | 7/2009 | Smith | ........................... | D26/108 |
| 8,202,259 B2 * | 6/2012 | Evans | ............... | A61M 39/0247 604/288.02 |
| 8,337,464 B2 | 12/2012 | Young et al. | | |
| 8,337,465 B2 * | 12/2012 | Young | .................... | A61M 1/14 604/175 |
| 8,409,228 B2 | 4/2013 | Blatter et al. | | |
| 8,414,530 B2 * | 4/2013 | Mason | ................ | A61M 1/3655 604/117 |
| 8,647,304 B2 * | 2/2014 | Axelsson | ................ | A61F 5/445 604/164.04 |
| 8,821,462 B2 * | 9/2014 | Axelsson | ................ | A61F 5/445 604/332 |
| 9,662,484 B2 * | 5/2017 | Woolley | ........... | A61M 39/0247 |
| 10,265,211 B2 * | 4/2019 | Bronnimann | .......... | A61F 5/449 |
| 10,702,688 B2 * | 7/2020 | Mason | ............. | A61M 39/0208 |
| 2001/0007931 A1 * | 7/2001 | Blatter | ................. | A61M 25/10 604/103.01 |
| 2003/0004520 A1 * | 1/2003 | Haarala | ............. | A61M 39/0247 606/108 |
| 2003/0139812 A1 * | 7/2003 | Garcia | ............... | A61B 17/1671 623/17.11 |
| 2009/0306599 A1 * | 12/2009 | Furuzono | .............. | A61L 29/106 604/175 |
| 2010/0274223 A1 * | 10/2010 | Teitelbaum | ....... | A61M 39/0208 604/507 |
| 2011/0184347 A1 | 7/2011 | Mason | | |
| 2011/0213309 A1 * | 9/2011 | Young | ................. | A61M 1/3661 604/175 |
| 2014/0243789 A1 | 8/2014 | Mehta et al. | | |
| 2019/0183660 A1 * | 6/2019 | Loring | .................. | A61F 2/4684 |

FOREIGN PATENT DOCUMENTS

| | | | |
|---|---|---|---|
| JP | 2012516223 | 7/2012 | |
| WO | WO2004033022 | 4/2004 | |
| WO | WO2007061100 | 5/2007 | |
| WO | WO2010011995 | 1/2010 | |
| WO | WO-2010109333 A2 * | 9/2010 | ........ A61M 39/0208 |
| WO | WO20111094712 | 8/2011 | |
| WO | WO2012064881 | 5/2012 | |
| WO | WO2014017986 | 1/2014 | |
| WO | WO2015085000 | 6/2015 | |
| WO | WO-2016111650 A1 * | 7/2016 | .......... A61M 1/3655 |

OTHER PUBLICATIONS

Hill, et al., Use of an Implantable Needle Guide to Access Difficult or Impossible to Cannulate Arteriovenous Fistulae Using the Buttonhole Technique, 14 J Vasc Access 164 (2013).
A New Solution in Av Fistula Access, Vital Access Corporation, (Sep. 8, 2013) http://www.vital-access.com/vwing/.
Notification of Reasons for Rejection dated Oct. 29, 2019 from Japanese Patent Application No. 2017-536309.
Notification of Reasons for Refusal dated Sep. 1, 2020 from Japanese Patent Application 2017-536309.

\* cited by examiner

SUBCUTANEOUS IMPLANTABLE DEVICE FOR GUIDING A VASCULAR ACCESS MEMBER AND METHOD FOR VASCULAR ACCESS

TECHNICAL FIELD

Embodiments relate generally to subcutaneous implantable device for guiding a vascular access member and method for vascular access.

BACKGROUND

End Stage Renal Disease (ESRD) is a debilitating and financially crippling chronic disease costing healthcare systems a staggering $67B annually to treat, incidence growing at an unmanageable rate. Hemodialysis (HD) is the predominant choice of treatment for 85% of ESRD patients. Ironically, as much as 38% of a patient's HD expenditure is not due to dialysis but vascular access. Vascular access remains the Achilles heel and one of the biggest unmet needs of HD.

There are 3 ways to obtain HD vascular access. Arteriovenous fistula (AVF) remains the gold standard with the lowest risk of complications. An arteriovenous graft (AVG) is the second option with shorter lifespan and higher risk of complication. A central catheter (CC) is often the last resort, meant only for temporary use with risk of serious complications leading to mortality. As such, preserving the health of an AVF, reducing the use of AVGs and CCs and their associated surgeries, is one of best strategy to reduce overall cost of ESRD.

Surveying the competitive landscape of the healthcare systems, there appears to be a gap in the area of preserving the health of the AVF, particularly during the "Wear & Tear" phase—i.e. the mid stage of an AVF lifespan after it is successfully created and matured, before onset of deterioration requiring repair interventions. During this stage, it is also noted that most number of preventable complications occurs due to poor cannulation.

Example embodiments provide an implantable device that seeks to address at least some of the issues identified above.

SUMMARY

According to various embodiments, there is provided a subcutaneous implantable device for guiding a vascular access member, the device including a channel defined by a through-hole in the device, wherein the channel is configured to guide the vascular access member therethrough to a vascular site; and anchoring means adapted for fixedly attaching, in a form of using suture, tissue in-growth, tissue encapsulation or tissue adhesion, the device to at least one of a dermis or a subcutaneous tissue at a position underneath the dermis to allow repeated access of the vascular access member through the channel to the vascular site, wherein the device is dimensioned to allow the device to be attached through the anchoring means for anchoring the entire device at a distance away from the vascular site.

According to various embodiments, there is provided a vascular access device for guiding a vascular access member, the device including a channel defined by a through-hole in the device, wherein the channel is configured to guide the vascular access member therethrough to a vascular site, and at least one subcutaneous anchor adapted to attach, in a form of using suture or tissue in-growth or tissue encapsulation or a tissue adhesion, the device to a subcutaneous tissue.

According to various embodiments, there is provided a method of creating scar tissue track for enabling low-skill and minimally painful vascular access, the method including implanting a permanent vascular access guiding device sub-dermally; anchoring the permanent vascular access guiding device in a fixed position; palpating the dermis to feel for the location and orientation of said permanent vascular access guiding device; finding the guiding channel of said permanent vascular access guiding device and accessing the guiding channel with a sharp vascular access member; following the angle of said guiding channel until the sharp vascular access member gain access the vascular site; repeating said palpating, finding and following steps until a scarred tissue track is created from under the dermis linking to the vascular site; and switching the sharp vascular access member to a blunt vascular access member to access the vascular site via said scarred tissue track.

According to various embodiments, there is provided a method of maintaining low-skill and minimally painful vascular access via scar tissue track, the method including performing the method of creating scar tissue track; palpating the dermis to feel for the location and orientation of said permanent vascular access guiding device; finding the guiding channel of said permanent vascular access guiding device and accessing the guiding channel with a blunt vascular access member; and following the angle of said guiding channel until the blunt vascular access member gain access the vascular site.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DETAILED DESCRIPTION

Embodiments described below in context of the apparatus device are analogously valid for the respective methods, and vice versa. Furthermore, it will be understood that the embodiments described below may be combined, for example, a part of one embodiment may be combined with a part of another embodiment.

It should be understood that the terms "on", "over", "top", "bottom", "down", "side", "back", "left", "right", "front", "lateral", "side", "up", "down", etc., when used in the following description are used for convenience and to aid understanding of relative positions or directions, and not intended to limit the orientation of any device, or structure or any part of any device or structure.

During the "Wear & Tear" phase of the life of an Arteriovenous fistula (AVF), Hemodialysis (HD) is typically conducted through the AVF. HD with AVF usually involves inserting needles into the AVF. The conventional cannulation techniques usually require rotation of cannulation sites between different dialysis sessions so as to avoid developing aneurysms. Recently, buttonhole (BH) cannulation technique has emerged as an alternative to the conventional cannulation techniques. The BH cannulation technique involves repeatedly inserting the needles into the exact same holes during every dialysis to create a tunnel track by the formation of scar tissue. BH, when executed correctly, may reduce common complications such as aneurysm, stenosis and hematoma. However, BH is today a technique only available to 5% to 15% of the population due to high skill barrier in executing BH creation, and in maintaining BH access.

Other conventional cannulation techniques may involve the use of vascular access ports, either percutaneous (sticking out of the skin) or invasive and indwelling in the vein. To implant such vascular access ports may risk damaging the blood vessel or cause massive bleeding or infecting the blood vessel. Thus, a perfectly sterile environment, such as an operating theatre is required for implanting such devices.

According to various embodiments, there is provided a subcutaneous implantable device that seeks to address at least some of the issues identified above.

Figure 1A:
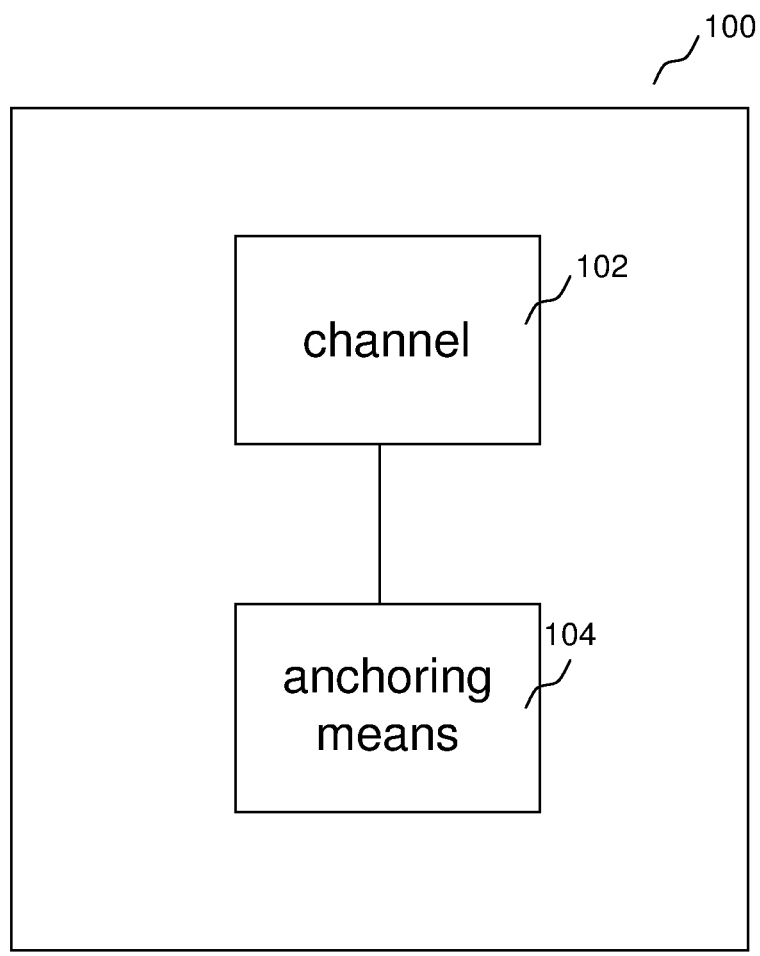
FIG. 1A-1B shows a schematic diagram of a subcutaneous implantable device for guiding a vascular access member according to various embodiments.

FIG. 1A shows a schematic diagram of a subcutaneous implantable device, for example a vascular access device, 100 for guiding a vascular access member, for example a fistula needle, according to various embodiments. The subcutaneous implantable device 100 may include a body. The subcutaneous implantable device 100 may further include a channel 102 defined by a through-hole extending through the body of the device 100. The channel 102 may be configured to guide the vascular access member therethrough to a vascular site, for example a site on the AVF, such that the vascular access member may cannulate the AVF. The device 100 may further include anchoring means 104 adapted for fixedly attaching, in a form of using a suture, tissue in-growth, tissue encapsulation or tissue adhesion, the device to at least one of a dermis or a subcutaneous tissue at a position underneath the dermis to allow repeated access of the vascular access member through the channel 102 to the vascular site. Accordingly, the subcutaneous implantable device 100 may be implanted underneath the dermis and may be fixed to the dermis or the subcutaneous tissue by the anchoring means such that the vascular access member may repeatedly be guided from a same entry point on the dermis through the channel 102 towards the AVF to cannulate the AVF at the same location or vascular site. The device 100 may be dimensioned to allow the device 100 to be attached through the anchoring means for anchoring the entire device 100 at a distance away from the vascular site. Accordingly, the device 100 may be shaped and dimensioned such that the device 100, when implanted underneath the dermis and attached to the dermis or the subcutaneous tissue, may not be in direct contact with the AVF, for example a layer of subcutaneous tissue may be present between the AVF and the device 100.

Embodiments of the subcutaneous implantable device 100 may consistently guide the vascular access member, for example a needle, without the device 100 touching a vein on which the vascular site may be located, and with the device 100 implanted under the skin. Embodiments of the device 100 may consistently guide the needle to penetrate the exact same spot of the skin, along the exact same angle across the subcutaneous tissue, to enter the exact same spot of the vein. This is very difficult to achieve and may only be executable by master skilled nurses manually and blindly for conventional buttonhole needling technique. However, this may be achieved by the device 100 in a way that the device 100 need not be attached to the vein. In other words, the device 100 may be non-invasive to the vein. The device 100 may also achieve the above in a way that the device 100 may be fully embedded under the skin, without anything penetrating through the skin. Accordingly, the device 100 may be advantageous in that it may allow unskilled cannulator to needle the exact same spot and angle without being able to see the device, for example even if the device may be hidden under the skin.

Advantageously, the subcutaneous implantable device 100 according to various embodiments may guide a vascular access member repeatedly to a constant site on a vessel, for example the AVF, without requiring the device 100 to be sutured or invasively attached onto the vessel. Accordingly, the subcutaneous implantable device 100 may not risk damaging the vessel or introducing infection etc. The subcutaneous implantable device 100 may also avoid causing the vessel to partially narrow. Further, the layer of subcutaneous tissue between the device 100 and the vessel may allow hemostasis when the vascular access member is removed, thus allowing the puncture on the AVF to close.

According to various embodiments, the anchoring means 104 may be adapted to fixedly attach the device 100 to the at least one of the dermis or the subcutaneous tissue for the channel 102 to consistently guide the vascular access member to repeatedly access a same location of the vascular site, via a same angle and via a same location of the dermis. In other words, when the device 100 is attached to the dermis or the subcutaneous tissue by the anchoring means 104, the anchoring means 104 may so fix the device 100 in a position underneath the dermis such that the device 100 may not move or migrate from the position. Accordingly, the vascular access member may access the device 100 repeatedly from a same location of the dermis and the device 100 may repeatedly guide the vascular access member along a same angle through the channel 102 to access a same location of the vascular site on the vein below the device 100, wherein the device 100 may not be in contact with the vein.

Figure 1B:
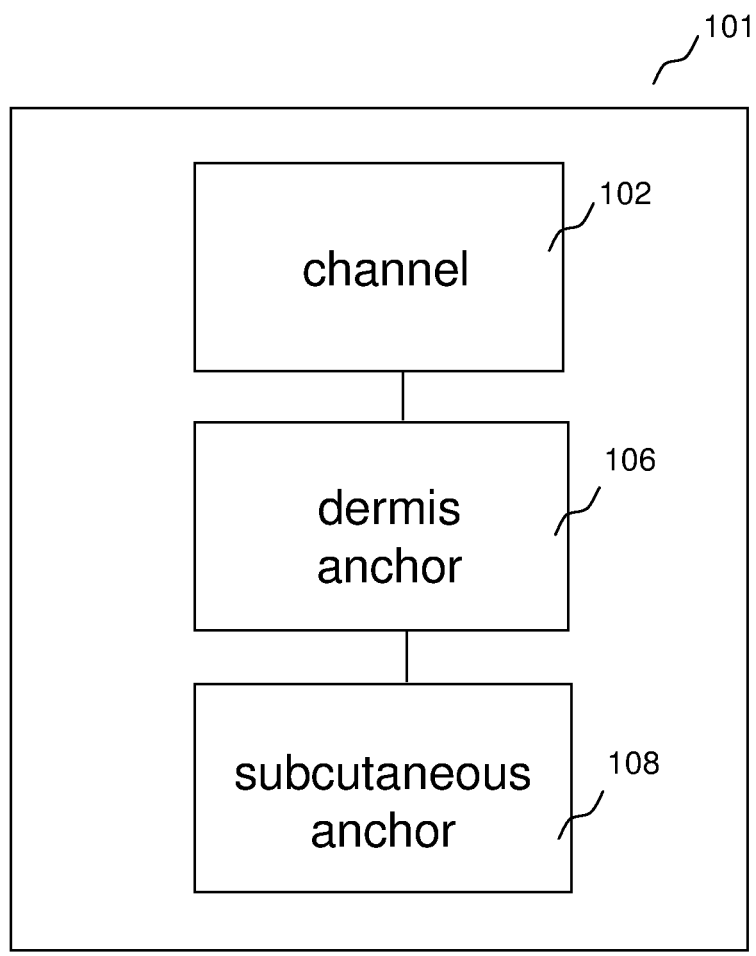

FIG. 1B shows a schematic diagram of a vascular access device 101 for guiding a vascular access member, for example a fistula needle, according to various embodiments. The vascular access device 101 may include a channel 102 defined by a through-hole in the device 101, wherein the channel 102 may be configured to guide the vascular access member therethrough to a vascular site. The device 101 may further include at least one subcutaneous anchor 108 adapted to permanently attach, in a form of using suture or tissue in-growth or tissue encapsulation or a tissue adhesion, the device 101 to a subcutaneous tissue. According to various embodiments, the device 101 may be directly attached to the subcutaneous tissue via the subcutaneous anchor 108.

According to various embodiments, the device 101 may further include at least one dermis anchor 106 adapted to temporary attach, in a form of using suture or tissue adhesion, the device 101 to a dermis.

Embodiments of the vascular access device 101 may be an implant or a vascular access implant. The device 101 may be used to guide needle to access a blood vessel. Embodiments of the device 101 may be configured to be anchored to the subcutaneous tissue only, hence need not be in direct contact or attachment to the vein on which the vascular site is located. In other words, the device 101 may be configured to be anchored to the subcutaneous tissue only in a way that need not be attached to the vein and is non-invasive to the vein. The device 101 may achieve the above through the dermis anchor 106, for example in the form of suture ports to suture the device 101 with the skin temporarily (for 1-8 weeks) so that the device 101 may be anchored within the subcutaneous tissue. The device 101 may then be permanently anchored to the subcutaneous tissue by the subcutaneous anchor 108, for example in the form of specially shaped and sized device 101 such that during the time the device 101 may be temporary anchored by the dermis anchor 106 subcutaneous tissue may optimally encapsulate the device 101 fully and trap or fix the device 101 in place. The device 101 may also be permanently anchored to the subcutaneous tissue by the subcutaneous anchor 108, for example in the form of tissue in-growth ports on the device for subcutaneous tissue to grow into the device 101 to integrate the device 101 and trap or fix the device 101 in place. The device 101 may also be permanently anchored to the subcutaneous tissue by the subcutaneous anchor 108, for example in the form of specially modified surface of the device 101 for the subcutaneous tissue to adhere better to the device 101 or to more securely anchor the device 101 to the subcutaneous tissue.

According to various embodiments, when the device 101 is implanted underneath the skin and after repeated use for guiding the vascular access member to access the vascular site, a scarred tissue track may be developed from under the skin, across an inner lumen of the device 101, leading to the blood vessel to be accessed. The scarred tissue track developed may further trap or fix the device 101 in place.

According to various embodiments, the temporary anchor, for example the suture, formed using the dermis anchor 106 may be removed after the subcutaneous anchor 108 has effectively anchor the device 101 to the subcutaneous tissue permanently.

According to various embodiments, the dermis anchor 106 may be adapted to fixedly attach the device 101 to the dermis at a position underneath the dermis, adjacent and non-invasive to the vascular site.

According to various embodiments, the subcutaneous anchor 108 may be adapted to fixedly attach the device 101 to the subcutaneous tissue at a position underneath the dermis, adjacent and non-invasive to the vascular site.

According to various embodiments, the subcutaneous implantable device 100 or the vascular access device 101 may include a top surface, an opposing bottom surface and a sidewall extending between the top surface and the opposing bottom surface, wherein at least a portion of the top surface and at least of a portion of the opposing bottom surface are spaced less than 6 mm apart from each other to enable the device to be implanted through an incision having a depth of less than 6 mm.

By having the distance between the top surface and the opposing bottom surface of the body of the device 100, 101 being less than 6 mm apart, the device 100, 101 may be implanted through an incision less than 6 mm deep from the skin. Essentially, a thinly shaped or dimensioned device 100, 101 may allow the device 100, 101 to be "slipped" under the skin through a shallow incision. It should be appreciated that there is a significant advantage in implanting a thin device 100, 101 (e.g., the device having a thickness of less than 6 mm) close to the skin in accordance with various embodiments. The shallow incision required for implanting the thin device 100, 101 may be away from blood vessels which may allow the incision to be easy to heal, thus making this procedure multiple times safer than implanting other implantable devices, for example taller and/or thicker implantable devices, which may require a deeper incision cutting into the blood vessels or direct invasive connections or attachments to the blood vessels. This significant advantage may translate into allowing implanting of the thin device 100, 101 to be performed in a treatment room rather than a full operating theatre which is required for implanting other implantable devices requiring deep incision. For implanting implantable devices requiring deep incision, a surgeon is required to perform the procedures in an environment that can cope with damages and bleeding to an important blood vessel (e.g., the AV fistula in this case) so as not to infect the blood vessel or deep lying tissue, thus a perfectly sterile environment such as an operating theatre is required. However, for implanting the device 100, 101 according to various embodiments, since the incision would be rather shallow from the skin, the risk profile may be rather low hence implanting the device 100, 101 may not need to be in the operating theatre environment. An operating theatre is considered the most expensive venue to book and hold a procedure in a hospital. Thus, by moving the procedure of implanting device 100, 101 out of the operating theatre, the device 100, 101 in accordance to various embodiments may also enable a significant cost reduction in implanting the device 100, 101 as compared to devices requiring deep incision. Hence, the thinly shaped or dimensioned configuration of the device 100, 101 as described in various embodiments may in fact distinguish device 100, 101 from other implantable devices and solves multiple problems, creating both clinical and cost impacts.

According to various embodiments, the top surface and the opposing bottom surface of the device 100, 101 may be substantially parallel to each other.

According to various embodiments, the opposing bottom surface of the device 100, 101 may be at least substantially flat. Advantageously, the flat bottom surface may allow normal compression of the layer of subcutaneous tissue, between the device 100, 101 and the vessel, onto the vessel so as to facilitate hemostasis of the punctured vessel beneath the device 100, 101, when pressure is applied normally on the skin above the device 100, 101.

According to various embodiments, the top surface of the device 100, 101 may include an identifiable portion for enabling an orientation of the device 100, 101 to be determined through tactile feel. When the device 100, 101 is implanted underneath the skin, it may be difficult to identify the orientation of the device 100, 101 and/or the entry point for the vascular access member. Advantageously, by having identifiable portion on the top surface of the device 100, 101 which may be felt through the skin, the orientation of the device 100, 101 and/or the entry point for the vascular access member may be found through tactile feel from the skin above the device 100, 101. According to various embodiments, identifiable portion may be in the form of the shape of the device 100, 101, such as triangular shape, elliptical shape or 'T' shape etc., for indicating the orientation of the device 100, 101, or distinct features such as corners, raised profiles, protrusions etc. for demarcating boundaries or orientation of the device 100, 101.

According to various embodiments, the top surface and the bottom surface of the device 100, 101 may be of the same shape.

According to various embodiments, the top surface and the bottom surface of the device 100, 101 may be elliptical, triangular, or "I"-shaped.

According to various embodiments, at least one of the top surface, the opposing bottom surface or the sidewall of the device 100, 101 may be sandblasted. Advantageously, by sandblasting the surface, the surface may be textured to be rough and uneven so as to enhance tissue adhesion. The enhanced tissue adhesion may facilitate the device 100, 101 for fixedly anchoring within the subcutaneous tissue.

According to various embodiments, the sidewall of the device 100, 101 may extend from the top surface of the device 100, 101 at a curve-edged interface. Advantageously, the curved-edged interface may prevent the device 100, 101 from expulsion through the skin or causing injury to the skin. The curved edge may also facilitate tissue encapsulation of the device 100, 101 after implantation, for example encapsulation of the device 100, 101 by the subcutaneous tissue.

According to various embodiments, the sidewall of the device 100, 101 may extend from the opposing bottom surface at a curve-edged interface. Advantageously, the curved-edged interface may prevent the device 100, 101 from expulsion into the vessel or causing injury to the vessel. The curved edge may also facilitate tissue encapsulation of the device 100, 101 after implantation, for example encapsulation of the device 100, 101 by the subcutaneous tissue.

According to various embodiments, the channel 102 of the device 100, 101 may have an inlet positioned on the top surface of the device 100, 101 through which the vascular access member enters, and an outlet positioned on the opposing bottom surface of the device 100, 101 from which the vascular access member exits. When the device 100, 101 is implanted underneath the skin and attached directly to the skin or the subcutaneous tissue, the inlet on the top surface of the device 100, 101 may be just beneath the skin such that the vascular access member may puncture the skin and enter into the inlet of the channel 102. The vascular access member may then be guided through the channel 102 and exit from the outlet on the opposing bottom surface of the device 100, 101. Upon exit from the outlet, the vascular access member may pierce through the subcutaneous tissue between the device 100, 101 and the vessel, and subsequently cannulate the vessel at a vascular site. With the device 100, 101 fixedly implanted in underneath the skin, the device 100, 101 may enable the vascular access member to cannulate the vessel at a consistent single location, along a consistent trajectory such that a single tunnel scarred track may be formed in the subcutaneous tissue between the device and the vessel.

According to various embodiments, a centre axis of the channel 102 may form an acute angle relative to the top surface of the device. Advantageously, with centre axis of the channel 102 forming an acute angle relative to the top surface of the device, the vascular site in which the vascular access member punctures the vessel may be outside the footprint of the device 100, 101. Accordingly, by applying normal direct pressure to the region on the skin, the subcutaneous tissue above the vascular site may cause hemostasis to close the punctured vascular site after the vascular access member is removed.

According to various embodiments, the acute angle may be about 5 degrees to about 45 degrees.

According to various embodiments, the channel 102 may have a substantially uniform diameter.

According to various embodiments, the subcutaneous anchor 108 of the device 101 may include an anchoring passage configured to allow the device 101 to be sutured to at least one of a dermis or a subcutaneous tissue at a fixed position and optionally, tissue in-growth therethrough. The anchoring passage may be a through hole across the device 101. The anchoring passage may include an aperture arranged coplanar with the top surface or an exterior surface of the sidewall. According to various embodiments, the subcutaneous anchor 108 of the device 101 may further include a plurality of anchoring passages.

According to various embodiments, the anchoring means 104 of the device 100 may include temporary anchoring means for anchoring the device 100 to the desire position immediately after the implant, and permanent anchoring means for long term attachment of the device 100 to the desired position. Advantageously, the permanent anchoring means may require time to be developed or formed, thus the temporary anchoring means may fix the device 100 at the desired position until the permanent anchoring means are developed or formed to fix the device 100. According to various embodiments, the anchoring means 104 may function to provide both temporary anchoring and permanent anchoring.

According to various embodiments, the anchoring means 104 of the device 100 may include an anchoring passage configured to allow the device 100 to be sutured to at least one of a dermis or a subcutaneous tissue at a fixed position and optionally, tissue in-growth therethrough. The anchoring passage may be a through hole across the device 100. Advantageously, the anchoring passage may function to provide both temporary anchoring and permanent anchoring. During implantation of the device 100, the device 100 may be sutured to the dermis or the subcutaneous tissue by threading through the anchoring passage. Accordingly, the anchoring passage may function as a dermis-anchor port in which suturing via the anchoring passage may immediately provide temporary attachment and or anchoring of the device 100 at the desired position. Overtime, the anchoring passage may allow tissue to in-grow through the entire anchoring passage. Thus, the anchoring passage may also function as a tissue in-growth port for permanently anchoring the device 100 at the desired position. By allowing tissue to in-grow through the entire anchoring passage, the device 100 may advantageously be better encapsulated within the subcutaneous tissue. Implant migration may also be minimized. With the long term anchoring in place, the sutures may then be removed or allowed to be dissolved.

According to various embodiments, the anchoring means 104 may include adhesive or biocompatible fasteners, for example tissue glue. The adhesive or biocompatible fasteners may function to temporary anchor the device 100 to the subcutaneous tissue. The device 100 may then be permanently anchored when the subcutaneous tissue grows to fully encapsulate the device 100.

According to various embodiments, the anchoring means 104 may be arranged on the sidewall of the device 100. Advantageously, arranging the anchoring means 104 on the sidewall may allow easy anchoring of the device 100 which is inserted underneath the skin. For example, when the anchoring means 104 include anchoring passage for manual suturing, the device 100 may be easily sutured from the exterior of the skin and across the device 100 such that the device 100 may be directly attached to the skin. When the anchoring means 104 include adhesive or biocompatible fasteners, the adhesive or biocompatible fasteners arranged on the sidewall may be easily attached to the subcutaneous tissue such that sideway movement of the device 100 may be prevented.

According to various embodiments, the anchoring means 104 may be arranged on the top surface. Advantageously, arranging the anchoring means 104 on the top surface may also allow easy anchoring of the device 100 which is inserted underneath the skin. For example, when the anchoring means 104 include automated suture ports loaded with sutures and needles, the device 100 may be easily sutured by triggering the sutures and needles to automatically deploy from the top surface vertically upwards to pierce through the skin for suturing to the skin. When the anchoring means 104 include adhesive or biocompatible fasteners, the adhesive or biocompatible fasteners arranged on the top surface may be easily attached directly to the skin from the beneath the skin, and the top surface may provide a relatively large surface area for adhesion.

According to various embodiments, the anchoring passage of the anchoring means 104 of the device 100 may include an aperture arranged coplanar with the top surface or an exterior surface of the sidewall. Accordingly, with the aperture of the anchoring passage of the anchoring means 104 arranged coplanar with the top surface, the anchoring means may be preloaded with sutures and needles which may be automatically deployed from the top surface vertically upwards to pierce through the skin for suturing the skin. With the aperture of the anchoring passage of the anchoring means 104 arranged coplanar with the sidewall, manual suturing may be easily performed by threading suture from the exterior of the skin and across the device 100 beneath the skin.

According to various embodiments, the aperture arranged coplanar with the sidewall may be sufficiently dimensioned such that the aperture may be easily located from outside the skin to facilitate manual suturing from the exterior of the skin while the device 100 is beneath the skin. Sufficiently dimensioned aperture may also facilitate in-grow of tissue for permanently anchoring the device 100.

According to various embodiments, the anchoring means 104 of the device 100 may include a plurality of anchoring passages. Advantageously, with a plurality of anchoring passages, the device 100 may be anchored more securely to the dermis or the subcutaneous tissue.

According to various embodiments, the device 100 may include at least one opening to allow tissue in-growth therethrough. Advantageously, in addition to anchoring means, the at least one opening may function to provide further permanent anchoring means to securely anchor the device to the subcutaneous tissue. The at least one opening may allow tissue to in-grow into the opening such that long term anchoring may be established. With the tissue in-growth through the at least one opening, the device 100 may be better encapsulated by the subcutaneous tissue thereby minimizing migration of the device 100.

According to various embodiments, the anchoring passage of the anchoring means 104 of the device 100 may be across a breadth of the device 100. Accordingly, the device 100 may be attached to the skin with suture across the breadth of the device 100.

According to various embodiments, the anchoring passage of the anchoring means 104 of the device 100 may be across a corner of the device 100. Accordingly, the device 100 may be attached to the skin with suture across the corners of the device 100. Advantageously, suture across the corners of the device 100 may provide additional stability against rolling of the device 100 about its longitudinal axis.

According to various embodiments, the device 100, 101 may include an orientation channel for verifying the orientation of the device 100, 101 with respect to the vessel prior to anchoring the device 100, 101 via the anchoring means 104. The orientation channel may be defined by a through-hole in the device 100, 101. The orientation channel may extend from the top surface of the device 100, 101 to the bottom surface of the device 100, 101. The orientation channel may be configured to guide a flashback needle therethrough to a target vessel such that the correct orientation of the device 100 may be confirmed by a successful flashback obtained upon cannulation of the target vessel by the flashback needle through the orientation channel.

According to various embodiments, the orientation channel may be perpendicular to the top surface of the device 100, 101. Accordingly, the orientation channel may be a vertical through-hole extending from the top surface of the device 100, 101 to the bottom surface of the device 100, 101.

According to various embodiments, the orientation channel may be parallel with the channel 102 for guiding the vascular access member. Accordingly, the orientation channel may be an angled through-hole.

According to various embodiments, the device 100, 101 may further include coupling means for removably coupling with a delivery device. The coupling means may couple the device 100, 101 to a delivery device such that the delivery device may be operated to insert the device 100, 101 through an incision on the skin and place the device 100, 101 at the desired position under the skin. Upon delivering the device 100, 101 to the desired position under the skin, the delivery device may be decoupled from the device 100, 101 so that the device 100, 101 may remain at the desired position under the skin while the delivery device may be removed. According to various embodiments, the coupling means of the device 100, 101 may be a female slot for receiving a male protrusion of the delivery device, or vice versa.

Accordingly, various embodiments may provide a subcutaneous implantable device for guiding a vascular access member. The device may include a channel defined by a through-hole in the device, wherein the channel is configured to guide the vascular access member therethrough to a vascular site; and an anchoring mechanism configured to anchor the device to the dermis and/or the subcutaneous tissue at a fixed position to allow repeated access through the channel to the vascular site, without the device invading into the vascular site. The device may further include a top surface, an opposing bottom surface and a sidewall extending between the top surface and the opposing bottom surface, wherein the top surface and the opposing bottom surface has a plurality of segments less than 6 mm apart to enable the device to be implanted through an incision less than 6 mm deep from the skin.

The device in accordance with various embodiments may distinguish from conventional access devices in that to solve the problem of guiding a needle to a constant site on a vein, the solutions provided by conventional access devices may typically require such conventional access devices to be sutured or to be invasively attached onto the vein. However, by doing so, other problems may be introduced. For example, firstly, such conventional access device may cause injuries/fatal damage to the vein if the conventional access device introduce infection and need to be explanted. Secondly, such conventional access device may run the risk of impeding hemostasis as there is no layer of subcutaneous tissue closing up the track when the needle is removed.

Thirdly, with such conventional access device fixated on the vein, it may run the risk of the conventional access device causing the vein to partially narrow. By choosing to anchor instead on the skin and the subcutaneous tissue above the vein, the device in accordance with various embodiments is provided to achieve the constant needle site outcome but yet avoid introducing the above mentioned problems.

In other words, the device in accordance with various embodiments may be configured specially to anchor to the dermis temporary, follow by the subcutaneous tissue permanently.

According to various embodiments, the features of the device configured for anchoring to the dermis may include through holes for sutures to wrap device onto skin, flat top to allow device to not create pointed stress points on skin, prominently rounded top edges (high radius fillet) to eradicate device erosion through the skin, and unique shapes (e.g. I/triangle/elliptical) for user to feel for the device and its orientation from the skin.

According to various embodiments, the features of the device configured for anchoring to the subcutaneous tissue may include through holes (can be the same ones shared with sutures) for subcutaneous tissue to in-grow through the entire device, prominently rounded edges (high radius fillet) to enable subcutaneous tissue to fully encapsulate the sub-device, sand blasted surfaces to increase tissue adhesion with the device as tissue proliferates across an undulating surface, and scarred track created by needling guided by device configured to form across the device, from under the dermis to the blood vessel. The scarred track may further prevent the device from migrating.

According to various embodiments, a method of creating a scar tissue track for enabling low-skill and minimally painful vascular access may include implanting a permanent vascular access guiding device, for example the implantable device or the vascular access device as described herein, sub-dermally; anchoring the permanent vascular access guiding device in a fixed position; palpating the dermis to feel for the location and orientation of said permanent vascular access guiding device; finding the guiding channel of said permanent vascular access guiding device and accessing the guiding channel with a sharp vascular access member; following the angle of said guiding channel until the sharp vascular access member gain access to the vascular site; repeating said palpating, finding and following steps until a scarred tissue track is created from under the dermis linking to the vascular site; and switching the sharp vascular access member to a blunt vascular access member to access the vascular site via said scarred tissue track.

According to various embodiments, a method of maintaining low-skill and minimally painful vascular access via a scar tissue track may include performing the method of creating the scar tissue track as described above; palpating the dermis to feel for the location and orientation of said permanent vascular access guiding device; finding the guiding channel of said permanent vascular access guiding device and accessing the guiding channel with a blunt vascular access member; and following the angle of said guiding channel until the blunt vascular access member gain access the vascular site.

Figure 2A:
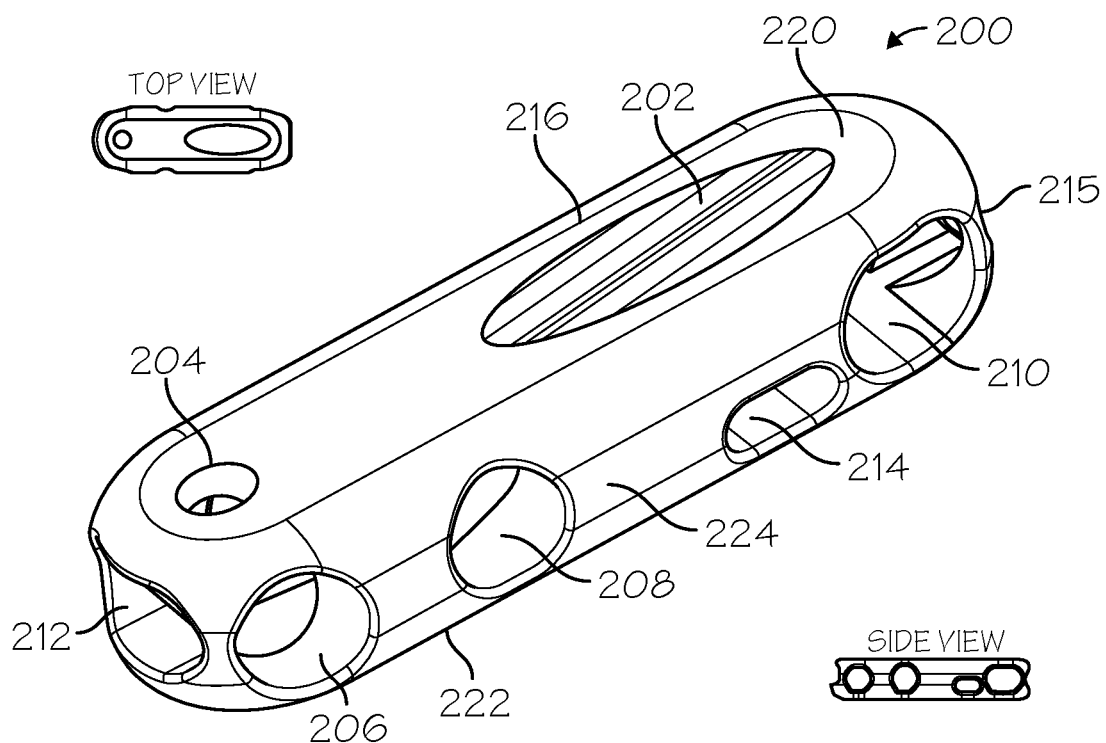
FIGS. 2A-2C show various embodiments of an implantable device configured to be implanted in the subcutaneous tissue for guiding a vascular access member.
Figure 2A:
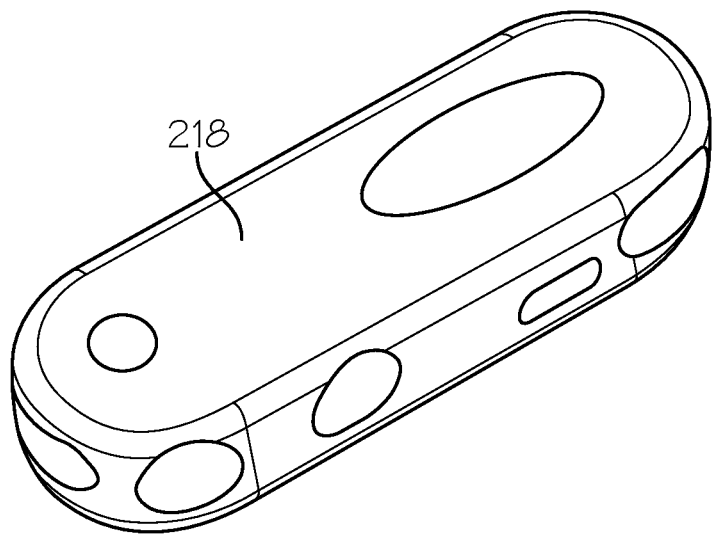
Figure 2B:
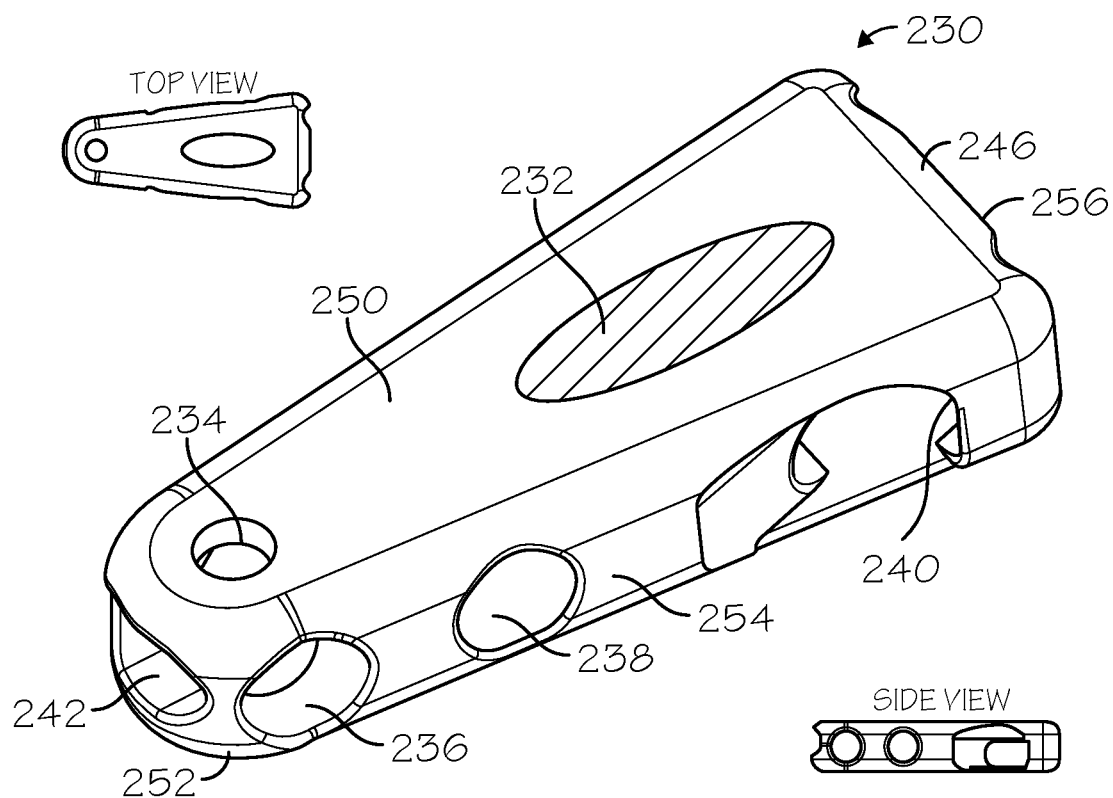
Figure 2B:
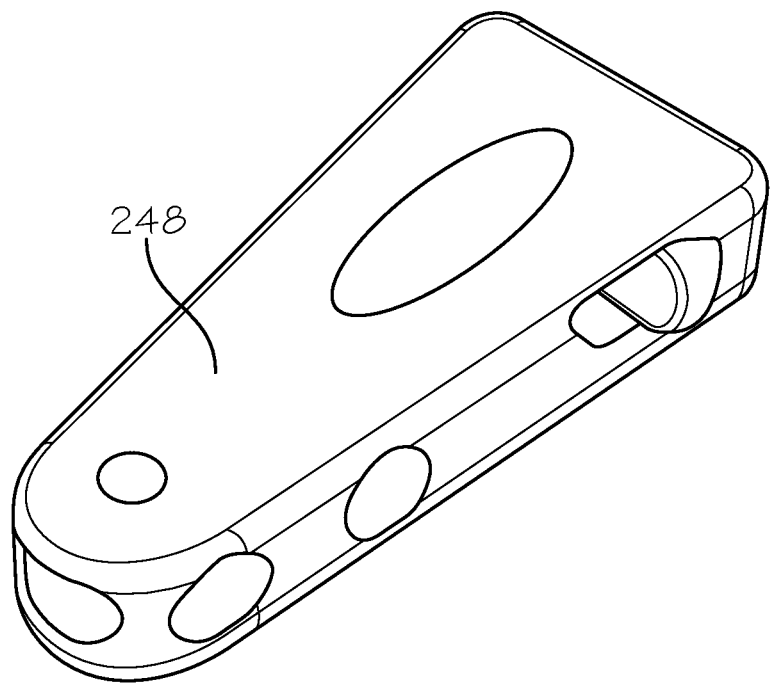
Figure 2C:
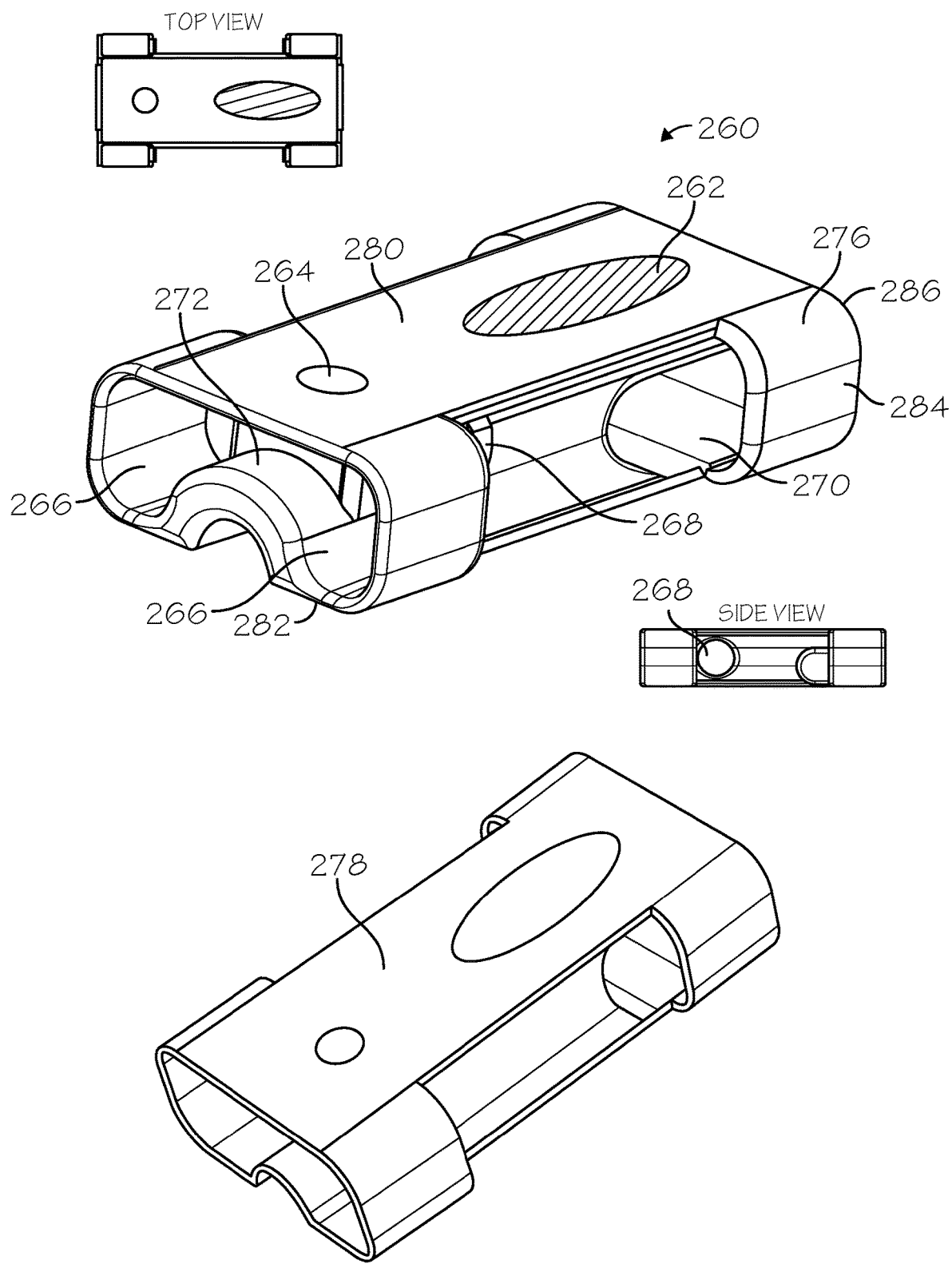

FIGS. 2A-2C illustrate various embodiments of a vascular access device (in other words an implantable device) 200, 230, 260 configured to be implanted in the subcutaneous tissue for guiding a vascular access member. The vascular access device 200, 230, 260 may also possibly be implanted in other types of tissue including though not limited to fats, dermis, muscle. The device 200, 230, 260 may temporarily be anchored to and from beneath the dermis in a way that is configured to guide a vascular access instrument, for example a sharp hemodialysis needle, to access a target vessel, for example an arteriovenous fistula/graft, that the device 200, 230, 260 is implanted above of but not in direct contact with. The device 200, 230, 260 may enable the vascular access instrument to cannulate the target vessel at a consistent single location, along a consistent angular trajectory in the tissue above the target vessel, such as the subcutaneous tissue. Over time, for example as soon as within 3 sessions spaced across 1 week, or within up to 10 sessions spaced across 4 weeks, a single tunnel scarred track may be formed from under the dermis, through the device 200, 230, 260, to and adhering to the target vessel. Once the scarred track is formed, the user may be able to switch from a sharp vascular access instrument, for example a rigid 17 G sharp needle, to a blunt vascular access instrument, for example a blunt buttonhole dialysis needle, to continue to access the target vessel. This is also upon which the process of infiltrating the skin and subcutaneous tissue to obtain vascular access along a scarred-down track of little nerve bundles becomes a less painful procedure. At this stage where a scarred buttonhole track is formed, the vascular access device 200, 230, 260 may then further reinforce as a shield to stop erroneous needling from piercing the subcutaneous tissue from the wrong skin entry point, thereby damaging the buttonhole track. The vascular access device 200, 230, 260 also at this stage protects the buttonhole track from being damaged by acting as a permanent guide against erroneous needling that cannulates from the correct skin entry point but at a wrong angle.

Each of said devices 200, 230, 260 shown in FIGS. 2A to 2C may be further configured to assume thin-profiled disc-liked architectures to specifically enable the device to maintain a distance, be it a thin layer of tissue, away from the target vessel. At the same time, said disc-liked profile configured with relatively flat top may enable the access device to be anchored to and from under the dermis with minimal risk of expulsion from the skin, and a relatively flat bottom surface to facilitate hemostasis of the post-punctured vessel that is beneath the device. The thin profile (for example approximately 1.5 mm-6 mm thickness) may further enable the device to be implantable via a low risk procedure that can be executed outside the operation theatre, such as the treatment room. Said procedure may require not more than a 6 mm deep incision in the subcutaneous tissue and not more than a 30 mm long incision on the skin to complete the implantation.

The devices 200, 230, 260 shown in FIGS. 2A to 2C may be further configured for its surrounding tissue, such as the subcutaneous tissue, to encapsulate the entire device 200, 230, 260, and anchor the device 200, 230, 260 in place with anchoring means such as a combination of tissue in-growth, scarring and/or adhesion mechanisms. Tissue in-growth mechanism may include through-holes that tissue can grow across the device 200, 230, 260. Scarring mechanism may include angular scarred-down buttonhole track deliberately created through the device 200, 230, 260. Adhesion mechanism may include sandblasted surfaces of the device 200, 230, 260 to promote tissue adhesion to the device 200, 230, 260. These anchoring mechanisms (in other words anchoring means) may enable the device 200, 230, 260 to be able to be locked in at a fixed position to accurately and consistently guide vascular access instruments, for example hemodialysis needles, to access the target blood vessel successfully, without the need to be fixated or integrated onto the target blood vessel. The anchoring mechanisms locking the device 200, 230, 260 in a fixed position may also be able to allow a high quality, single-tunnel buttonhole track to be formed below the device 200, 230, 260, and may allow the buttonhole track to form faster (for example as fast as 1-2 weeks) than current manual blind technique performable only by skilled master nurses. In addition to the above subcutaneous tissue anchoring mechanisms, the device 200, 230, 260 may also be configured with anchoring means such as a plurality of strategically placed suture ports for the device 200, 230, 260 to be temporarily sutured to the dermis for 1 to 4 weeks, this acting as a transition anchor before the long-term subcutaneous tissue anchoring takes over.

The devices 200, 230, 260 shown in FIGS. 2A to 2C may be further configured to have all their edges significantly rounded, for example at between 0.75 mm to 1.5 mm fillet radius, to mitigate expulsion through the skin, mitigate creating stress points leading to injury to the blood vessel beneath the device 200, 230, 260, and to facilitate complete tissue encapsulation around the device 200, 230, 260 to anchor the device 200, 230, 260. The vascular access device 200, 230, 260 may be made from medical grade metals such as though not limited to titanium alloys, stainless steel, cobalt chrome, etc, or from medical grade polymers, such as though not limited to polytetrafluroethylene (PTFE/Teflon), polyetheretherketone (PEEK), Polypropylene, or dissolvable PLGA/PLLA (poly-lactic-co-glycolic acid, polylactic acid), etc.

FIG. 2A shows an isometric view, a side view, a top view and a photograph of the vascular access device 200 according to various embodiments. As shown, the device 200 may be a thin-profiled, elliptical-shaped disc implantable device 200.

The device 200 may be shaped in a thin disc liked profile between 1.5 mm to 6 mm in height to facilitate implantation of the device 200 right under the skin with an incision not deeper than 6 mm. Accordingly, the device 200 may include a top surface 220, an opposing bottom surface 222 and a sidewall 224 extending between the top surface 220 and the opposing bottom surface 222, wherein at least a portion of the top surface 220 and at least of a portion of the opposing bottom surface 222 are spaced less than 6 mm apart from each other to enable the device to be implanted through an incision having a depth of less than 6 mm.

As shown, the device 200 may be shaped elliptically for user to determine the direction which the needle should enter the device.

The device 200 may include two working channels 202, 204 and six anchoring ports 206, 208, 210, 212, 214, 215 for a variety of purposes.

The device 200 may include a first channel or an access channel 202 defined by a through-hole from the top 220 of the device 200 to the bottom 222 of the device 200. The access channel 202 may be the largest hole in the device 200.

The access channel 202 may be at a fixed angle between 5-45 degrees with respect to the top 220 or bottom 222 of the device 200. The opening of the access channel 202 at the top 220 of the device 200 may be an entry point (in other words an inlet) for a needle. The diameter of the access channel 202 may allow for a range of 15 G to 17 G dialysis needle to enter. The purpose of the access channel 202 may be to guide a dialysis needle through the channel 202, with an end (in other words an outlet) of the channel 202 leading towards the target vessel, for example a AV fistula, for creating a buttonhole track through the subcutaneous tissue between the implanted device 200 and the target vessel.

The top 220 of the device 200 may include a flat top surface. With the flat top surface 220, the device 200 may not create stress points on the skin when implanted. Thus, the flat top surface 220 may mitigates expulsion from skin.

The device 200 may include a second channel or an orientation channel 204 for verifying the orientation of the device 200 with respect to the target vessel during implantation. The orientation channel 204 may be a vertical through-hole from the top 220 of the device 200 to the bottom 222 of the device 222. The orientation channel 204 may be configured to accommodate a flashback needle with a maximum size of up to 20 G. The orientation channel 204 may be accessed during implantation procedure to test and ascertain accurate orientation of the device 200 with respect to the target vessel, for example the AV fistula. Orientation may be confirmed by a successful flashback obtained upon cannulation of the target vessel. Accordingly, the orientation channel 204 may function as a vertical targeting needle hole which can accommodate up to 20 G needle.

The device 200 may include anchoring means. The anchoring means may include dermis-anchor ports 206, 208, 210 for anchoring the device to the dermis from beneath the skin, as a form of transition anchor before long-term subcutaneous anchoring takes over. In this embodiment, there are three dermis-anchor ports 206, 208, 210 created as a form of enlarged or sufficiently dimensioned through-holes across the breadth-wise for easy suturing across the breadth of the implanted device 200. The through-holes may function as anchoring passages in which suture may be threaded through. The dermis-anchor ports 206, 208, 210 may be enlarged or sufficiently dimensioned for the following purposes. To facilitate suturing when the device 200 is hidden under the skin as the surgeon needs to find the dermis-anchor ports or suture ports 206, 208, 210 blindly, i.e. without visually seeing the suture ports 206, 208, 210 as the device is implanted beneath the skin. To provide plenty of room after the suture is threaded through, to allow subcutaneous tissue to in-grow or grow across through the entire through-hole or anchoring passages of the dermis-anchor ports 206, 208, 210 as a way to permanently anchor the implanted device 200 with the subcutaneous tissue. Accordingly, the dermis-anchor ports 206, 208, 210 may function as holes 206, 208, 210 that allow tissue growth across the implanted device 200. In this way, the implanted device 200 may be better encapsulated and subsequent migration of the implanted device 200 may be minimized. In this embodiment, a maximum of 3 sutures may be applied to the three dermis-anchor ports for securing the device 200 to the dermis.

The device 200 may include tissue in-growth ports 212, 214, 215 to promote tissue in-growth into and/or across the device 200 when implanted, particularly the subcutaneous tissue that surrounds the implanted device 200. The tissue in-growth ports 212, 214, 215 may be smaller than the dermis-anchor ports 206, 208, 210. The tissue in-growth ports 212, 214, 215 may also be considered as anchoring means because the tissue in-growth ports 212, 214, 215 is one of the mechanisms for establishing long term anchoring of the implanted device 200 to the subcutaneous tissue after the sutures are removed/dissolve. Accordingly the tissue in-growth ports 212, 214, 215 may function as additional holes to promote tissue growth into the implanted device 200 for anchoring. The tissue in-growth ports 212, 214, 215 may also enable better encapsulation and minimize implanted device 200 migration.

The device 200 as shown in FIG. 2A may have all its edges curved 216 with fillet of radius between 0.75 mm to 1.5 mm. This may prevent the device 200 from expulsion through the skin, or into the AV fistula, or having sharp edges that could injure the AV fistula or the skin. The rounded edges 216 may also facilitate tissue encapsulation of the device 200. Accordingly, the curved edges 216 may mitigate implant expulsion from skin and promote full tissue encapsulation around the implanted device 200. Thus, the rounded edges 216 may be considered as one of the long term anchoring mechanisms to anchor the implanted device 200 to the subcutaneous tissue.

As shown in the photographs of the device 200 in FIG. 2A, all exterior surfaces of the device may be sandblasted. This may increase tissue adhesion to the device 200 and mitigate device 200 migration. This is because sandblasted outer surfaces 218 may create rough surfaces that promote tissue encapsulation and tissue adhesion to the device 200. Thus, the sandblasted surfaces 218 may also be considered means to anchor the device 200 with the subcutaneous tissue and prevent migration.

FIG. 2B shows an isometric view, a side view, a top view and a photograph of the vascular access device 230 according to various embodiments. As shown, the device 230 may be a thin-profiled, triangular-shaped implantable device 230.

The device 230 in FIG. 2B may include similar features as the device 200 as shown in FIG. 2A. For example, the device 230 may include access channel 232, orientation channel 234, tissue in-growth port 242, the rounded edges 246 and sand blasted surfaces 248, which correspond with similar features found in device 200 in FIG. 2A.

The device 230 may differ from the device 200 of FIG. 2A in that the device 230 may include a triangular shaped surface. The triangular shape may be an isosceles triangle. The triangular shape may provide the additional advantage of conferring direction to the implanted device 230, and allows for tactility to eliminate cannulation error after implantation. For example, the apex of the isosceles triangle may indicate the direction of needle cannulation. Accordingly, the triangular shaped implantable device 230 may enable user to determine orientation of the device 230 and needling direction through tactile feel from the skin.

The device 230 may further differ from the device 200 of FIG. 2A in that the dermis-anchor ports 240 at the proximal end are larger holes and are located at the two corners of the base of the isosceles triangular shaped device 230. Said two proximal ends dermis-anchor ports 240 may be configured for sutures to anchor the device 230 around the corners of the device 230, instead of across the breadth like dermis-anchor port 210 of the device 200 of FIG. 2A. With this change, the device 230 as shown in FIG. 2B may utilize a maximum of four suture anchors 236, 238, 240, and may provide additional stability against rolling along a longitudinal axis of the device 230 via the two corners dermis-anchor sutures. Thus, the triangular shaped implantable device 230 may also enable a more stable 3-points suture anchor on the skin done at the 3 corners of the triangle.

The device 230 may further differ from the device 200 of FIG. 2A in that the device 230 may include a rectangular inlet (in other words coupling means) 256 at the proximal end of the device 230, between the two corner dermis-anchor ports 240. Said rectangular inlet 256 may be a female slot to snap fit a male attachment of a deployment instrument (not shown) that facilitates the implantation of the device 230. The rectangular inlet 256, acting as a female slot, allows said device to benefit for quick attachment and release from a deployment instrument to enhance the stability of the device 230 during the implantation into the subcutaneous tissue.

FIG. 2C shows an isometric view, a side view, a top view and a photograph of the vascular access device 260 according to various embodiments. As shown, the device 260 may be a thin-profiled "I"-shaped implantable device 260.

The device 260 in FIG. 2C may include similar features as the device 200 as shown in FIG. 2A and the device 230 as shown in FIG. 2B. For example, the device 260 may include access channel 262, orientation channel 264, tissue in-growth port 272, rounded edges 276 and sand blasted surfaces 278, which correspond with similar features found in device 200 in FIG. 2A and device 230 in FIG. 2B. Further, device 260 may include female inlet 286 that mates with a delivery instrument for stability during implantation procedures, similar to the female inlet 256 of the device 230 in FIG. 2B.

The device 260 may differ from the device 200 of FIG. 2A and the device 230 of FIG. 2B in that the device 230 may include "I" shaped surface.

The device 260 may further differ from the device 200 of FIG. 2A and the device 230 of FIG. 2B in that the dermis-anchor ports 266, 270 at both ends of the device 260 may be highly enlarged to allow four suture points on each of the four corners of the "I" shaped device 260. The four corners dermis-anchor ports 266, 270 may be configured for sutures to be sutured parallel to the longitudinal axis of the device 260, around the protruded "I" beams. One dermis-anchor port 268 may run across the breadth of the device 260, similar to the dermis-anchor port 208 in the device 200 of FIG. 2A.

Figure 3:
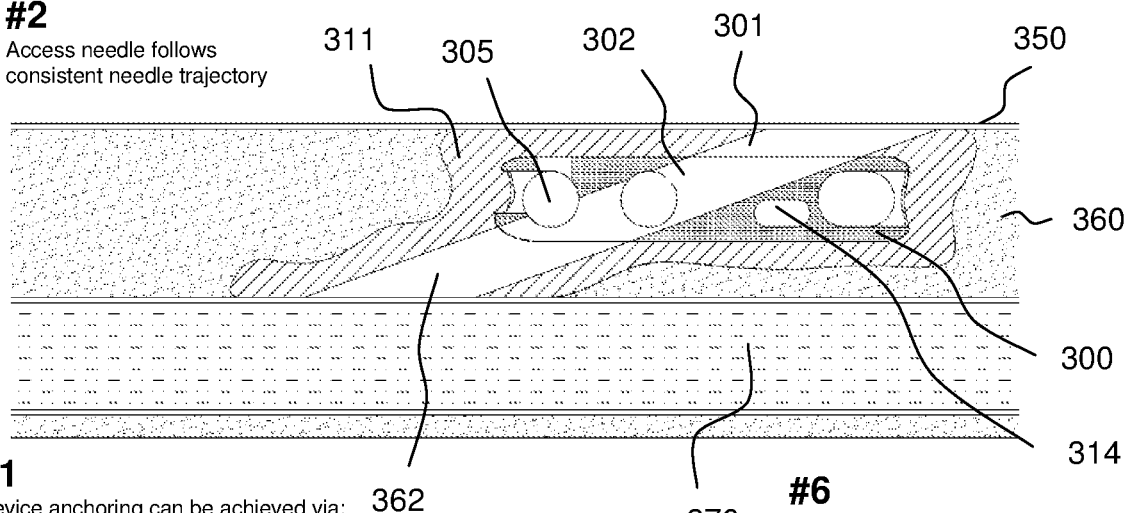
FIG. 3 shows an implantable device implanted in a subcutaneous tissue underneath a skin according to various embodiments.

FIG. 3 shows an implantable device 300 according to various embodiments implanted in a subcutaneous tissue underneath a skin.

As shown in FIG. 3, the device 300 may be held in place by the subcutaneous tissue 360 via the tissue in-growth channels 314. The device 300 may not be attached to a vein or an AV Fistula (AVF) 370. In other words, the device may not be touching the vein or the AVF 370. The bottom of the device 300 may be deliberately configured to be flat to aid hemostasis, which will be described later with reference to FIG. 4. An exit point of a needle lumen or a channel may be at a corner of the device 300 to direct the needle to pierce the vein at a vascular site, which is not directly under the device 300. This may further aid hemostasis, which will be described later with reference to FIG. 4. The device 300 as shown may be flat on the top and fully embedded under the skin. In other words, there is nothing percutaneous protruding out of the skin that could promote infection. As shown in FIG. 3, a buttonhole scared track may be made from the aid of the device 300 that runs across the device 300 to the vein. The device 300 may also be elliptical in shape so that when a nurse or a patient feels for the boundaries of the device 300, it may know which direction to perform the needling. The boundaries of the device 300 may also be optimally round edged such that the device 300 may be prevented from eroding through the skin. This may also optimize the tissue encapsulation for the subcutaneous tissue to scar around the device 300 and trap or fix the device 300 in place. The device 300 may be sandblasted to promote tissue adhesion to anchor the device 300 in place within the subcutaneous tissue. The device 300 may be configured with the thinnest possible disc profile to enable the device 300 to be implanted under the skin, without the need of being performed in an operating theatre and/or under anesthesia.

Various functions of the implanted vascular access device 300 and the unique ways it interacts with the surrounding tissue(s) and vasculature(s) will be described in the following.

As shown in FIG. 3, the device 300 may always be implanted with an entry point 301 of the cannulation channel 302 proximal to the skin 350, with the direction of cannulation away from the device entry incision site (not shown).

As shown in FIG. 3, the device 300 may be anchored in the subcutaneous region 360 by transition sutures 305 and long-term encapsulation 311 of the device 300. The sutures 305 may anchor the device 300 to the skin 350 for 5-14 days. Thereafter, the device 300 may be anchored long-term by surrounding subcutaneous tissue 360 encapsulating the device with fibrosed tissue 311. This fibrous capsule 311 may be enhanced through deliberately configured anti-migration channels, for example tissue in-growth port 314, and promoted through surface modification, for example sandblasted surface.

As can be understood from FIG. 3, with the device 300, the entering access needle may be enabled to traverse in an optimal consistent trajectory towards the AV Fistula (AVF) 370.

As shown in FIG. 3, through regular cannulation of sharp needles through the device 300 during initial dialysis sessions, a buttonhole track 362 may be formed as early as two weeks. This leaves behind a scarred track 362 leading to a scarred entry flap (not shown) of the vessel. Subsequently, the track 362 formed may be cannulated via a blunt needle.

As can be understood from FIG. 3, with the guidance of the device 300, the cannulation with both sharp and blunt needles may leave a precise track 362 of high quality. Buttonhole track 362 created by the device 300 may consistently be a single precinct track 362, instead of a track with multiple "branches" that often occurs if Buttonhole track creation is done manually and/or blindly.

As can be understood from FIG. 3, the device 300 may also be able to lower the technical skill requirement of creating buttonhole track 362, thus allowing renal nurses of varying technical skills to create the buttonhole track 362 and access the AV fistula via the device 300 with more confidence. The device 300 may further empower patients themselves, or their family members who are non-medically trained, to cannulate the AVF 370 with confidence at home or outside the dialysis centre.

As can be understood from FIG. 3, the device 300 may also be able to achieve hemostasis with no changes to the current compression technique. This will be further described with reference to FIG. 4.

Figure 4:
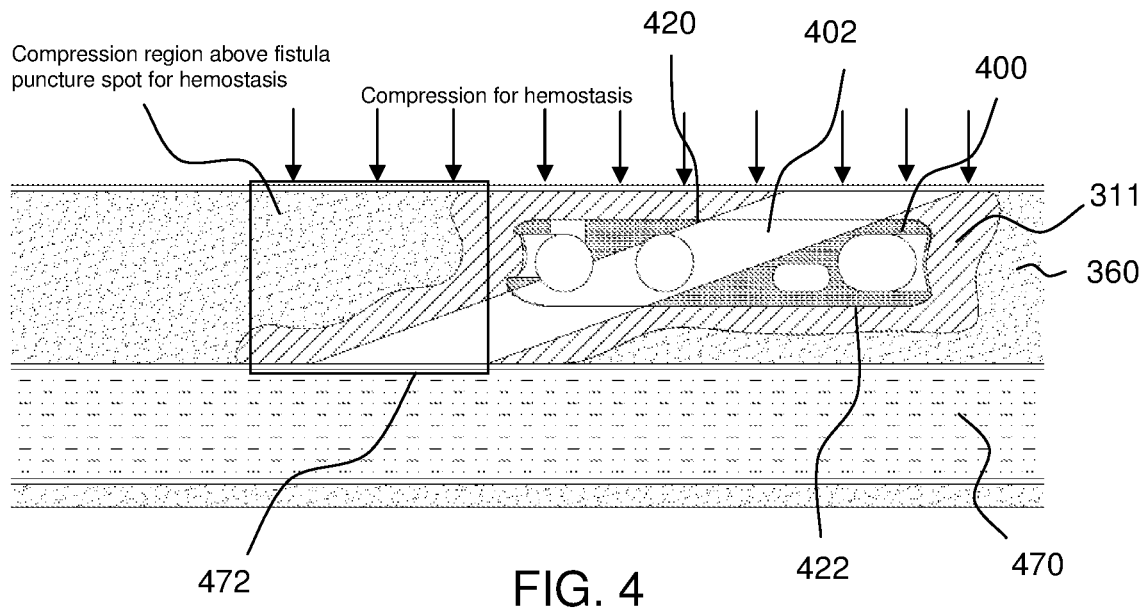
FIG. 4 shows implantable device implanted in a subcutaneous tissue underneath a skin according to various embodiments.

FIG. 4 shows an implantable device 400 according to various embodiments implanted in a subcutaneous tissue underneath a skin. Hemostasis of the vasculature post-cannulation will be described in the following.

The device 400 may be configured intentionally to aid hemostasis of the vasculature post-cannulation. The device 400 may include channel 402 with a centre axis of the channel 402 forming an acute angle of approximately 20 degree relative to a top surface 420 of the device 400 such that the nurses may cannulate the AV fistula 470 at an optima angle of 20 degree. Accordingly, the needle venipuncture site or the AVF puncture spot 472 may be outside the footprint of the device 400. Therefore, when a normal direct pressure is applied to the region similar to what is currently practiced post dialysis for hemodialysis, hemostasis may occur to close the puncture 472.

According to various embodiments, the base or the bottom surface 422 of the device 400 may be flat. Accordingly, when normal pressure is applied to the skin, the base or the bottom surface 422 of the device 400 may function to translate the normal compression from the skin to the AVF 470 such that hemostasis may occur. In other words, the base or the bottom surface of the device may exert normal compression on the AVF 470 for hemostasis when pressure is applied normally.

As shown in FIG. 4, the device 400 may be configured or dimensioned such that when implanted beneath the skin, a layer of subcutaneous tissue may be between the device 400 and the AVF 470. The layer of subcutaneous tissue between the device 400 and the AVF 470 may apply a distributed pressure across the puncture spot, preventing blood flow out to the subcutaneous tissue so that hemostasis may occur to close the puncture spot 472.

FIGS. 5A to 5H illustrate a method of implanting the vascular access device (in other words the implantable device) 500 and the process of preparing the implanted device 500 for blunt needle cannulation according to various embodiments.

Figure 5A:
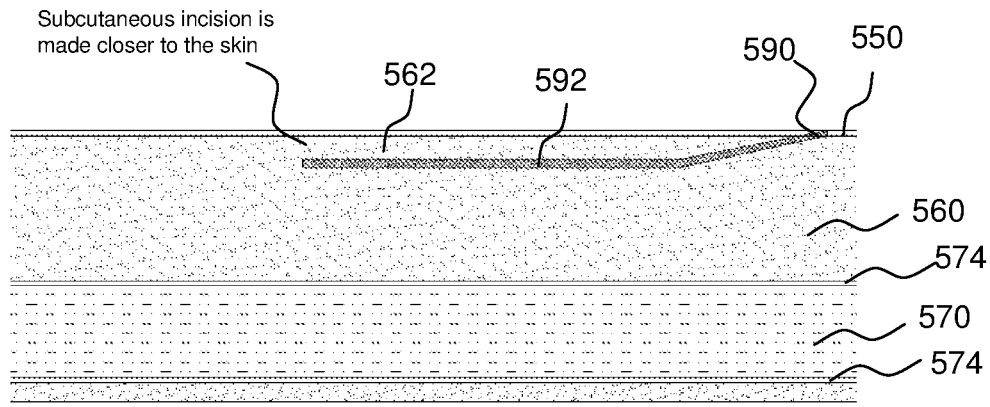
FIGS. 5A to 5H illustrate a method of implanting an implantable device and the process of preparing the implanted device for blunt needle cannulation according to various embodiments.

As shown in FIG. 5A, a cut down incision 590 between 1 cm to 3 cm long may be created on the skin. The incision 590 may allow access to the space below the dermis 550 and below a thin layer of subcutaneous tissue 562. A tunnel 592 along the subcutaneous tissue 560 may be created, and said tunnel 592 may be approximately 2-3 mm below the skin, running parallel with the AV fistula 570 in the longitudinal direction. As shown, fistula walls 574 separate the fluid in the AV fistula 570 from the subcutaneous tissue 560.

Figure 5B:
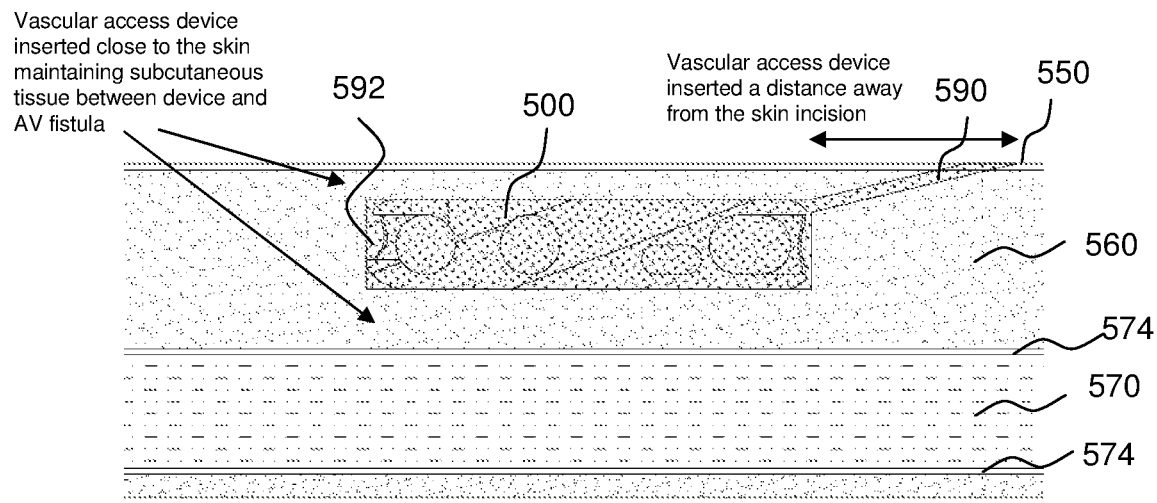

As shown in FIG. 5B, the device 500 may be inserted into the incision 590, and slipped along and into the subcutaneous tissue tunnel 592.

Figure 5C:
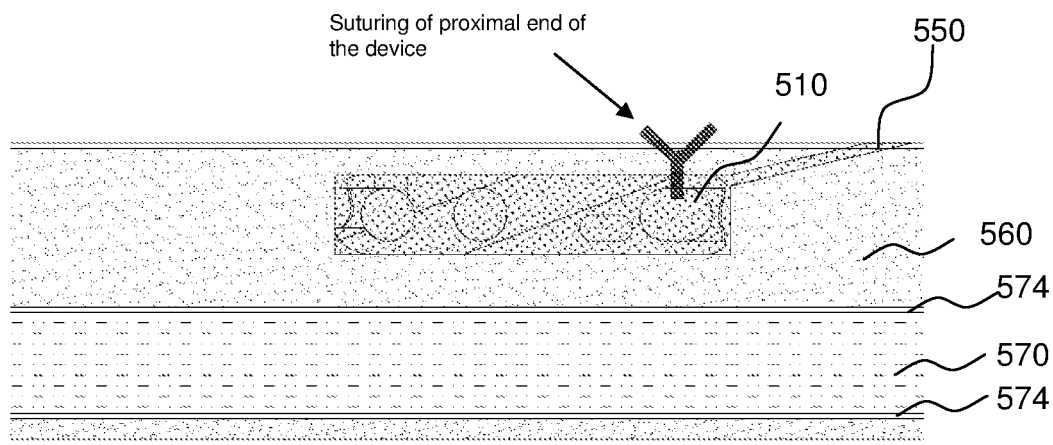

As shown in FIG. 5C, a proximal end of the device 500 may be sutured onto the skin 550 via anchoring means such as dermis-anchor port 510.

Figure 5D:
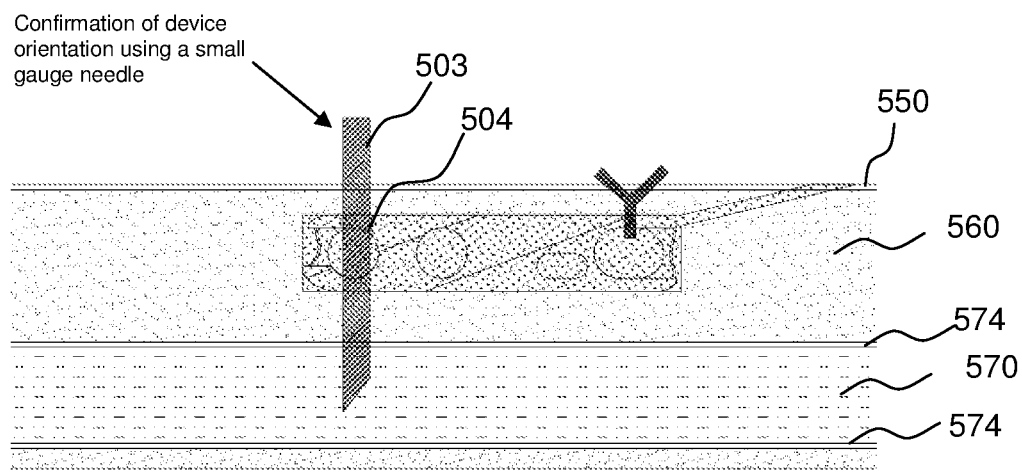

As shown in FIG. 5D, the orientation of the device 500 may be confirmed by using a small test needle 503 such as 21 G to 25 G sized, to access the AVF 570 via orientation channel 504. The orientation of the device 500 may be confirmed upon seeing blood flash back in the test needle 503.

Figure 5E:
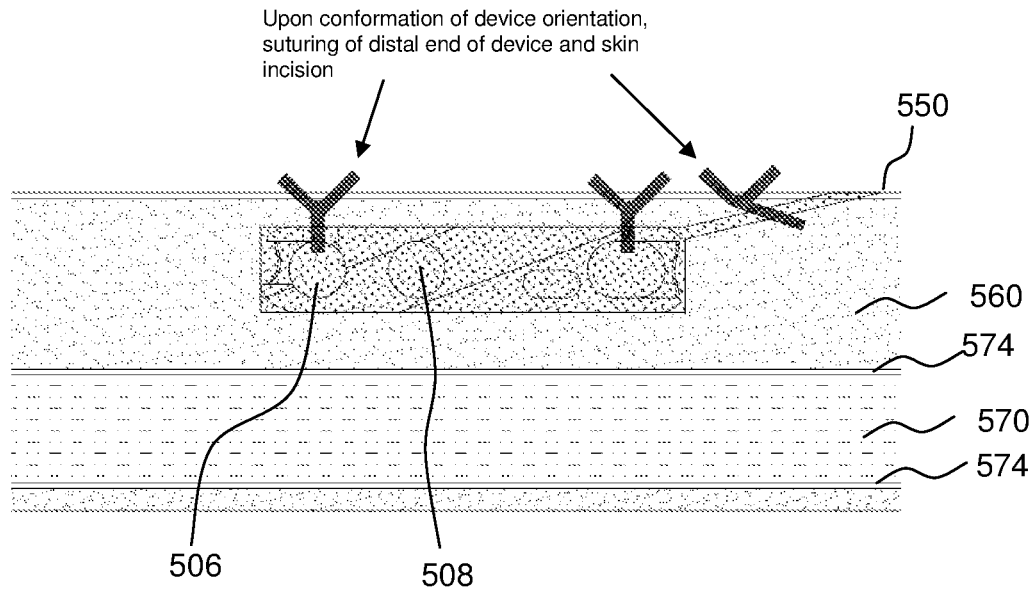

As shown in FIG. 5E, upon confirmation of the orientation of the device 500, the distal end or remaining suture ports 506, 508 of the device 500 may be sutured. The incision site 590 may also be sutured closed for healing.

Figure 5F:
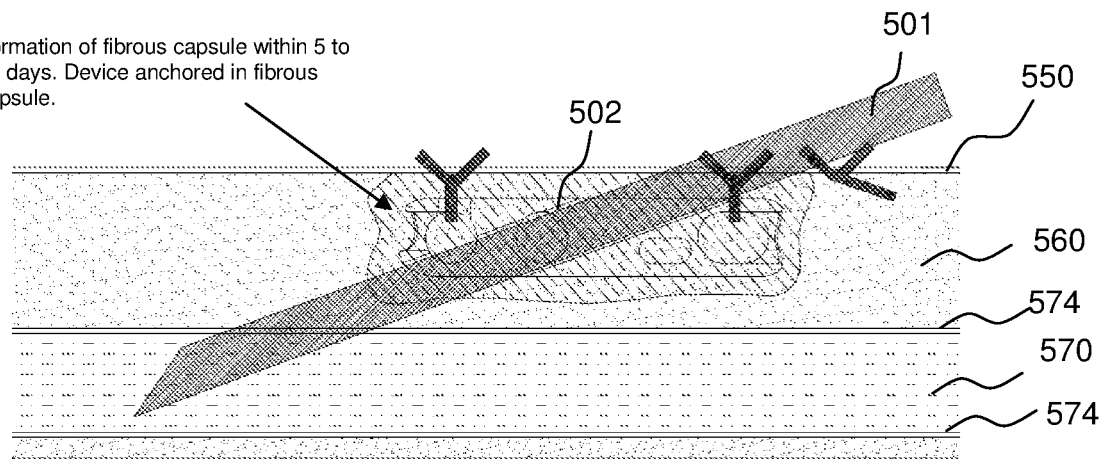

As shown in FIG. 5F, after 5-14 days, the device 500 may be firmly anchored to the subcutaneous tissue 560 via tissue encapsulation, tissue in-growth into the device 500 and tissue adhesion to the device 500 surfaces. Cannulation of the AVF 570 may be performed for commencing dialysis. The skin sutures may also be removed at this point if the user wishes to. To cannulate the AVF 570 using the implanted device 500, the user may follow the three steps: feel it, find it, and follow it.

Feel it: user may feel for the device 500 beneath the skin by means of sensing using their fingers to locate the boundary of the device 500.

Find it: using a recommended dialysis needle 501, user may find the location of the access device lumen. The direction for insertion of needle 501 may be away from the incision scar.

Follow it: Once the dialysis needle 501 is in the lumen, user may just follow the direction of the guide or the channel 502 and push the needle in slowly until flashback may be observed, indicating the needle 501 has successfully obtained access to the AV fistula.

The three steps above are further shown and described later with reference to FIGS. 6A to 6D.

Once dialysis is completed, needle 501 may be removed and pressure may be applied on the area to achieve hemostasis as per usual practice.

Figure 5G:
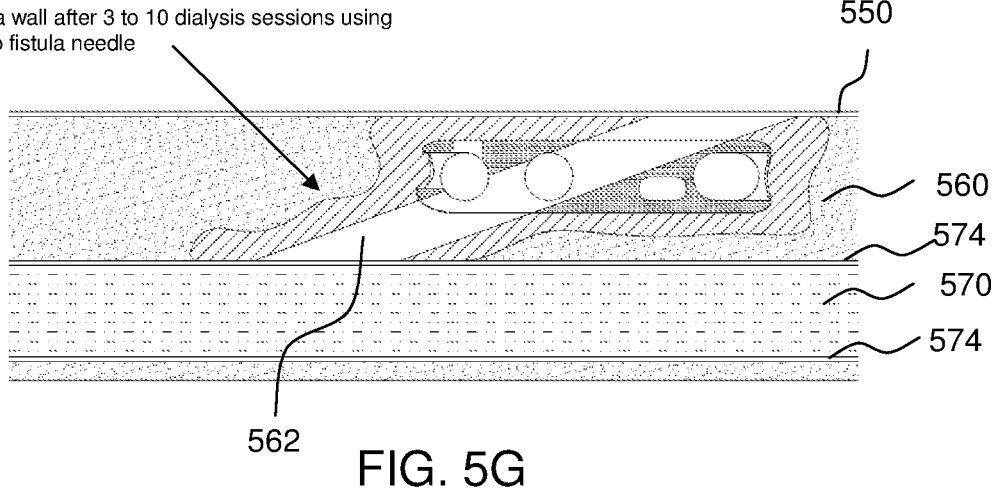

As shown in FIG. 5G, after 3 to 10 dialysis sessions, i.e. 1 to 4 weeks respectively, due to the consistent needle trajectory enabled by the channel 502 of the device 500, a buttonhole track 562 starting from under the skin 550, across the device 500, through the subcutaneous tissue 560, to and sticking to the AV fistula 570 may be formed.

Figure 5H:
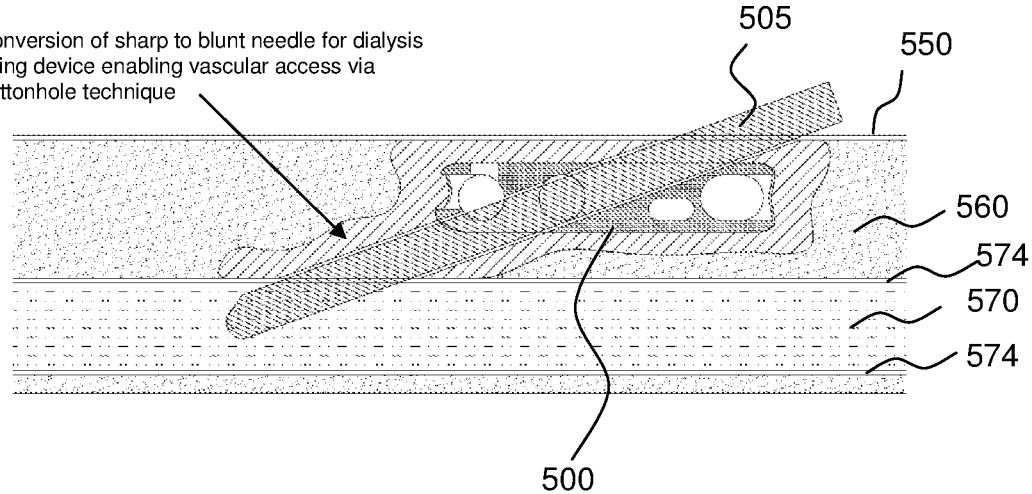

As shown in FIG. 5H, after the buttonhole track 562 is successfully created, the user may switch to utilizing a blunt dialysis needle 505 to perform vascular access and dialysis. To use the blunt dialysis needle 505 with the device 500, the same three steps of "feel it", "find it" and "follow it" may be applicable.

FIGS. 6A to 6D show photographs of the Feel, Find and Follow procedure.

Figure 6A:
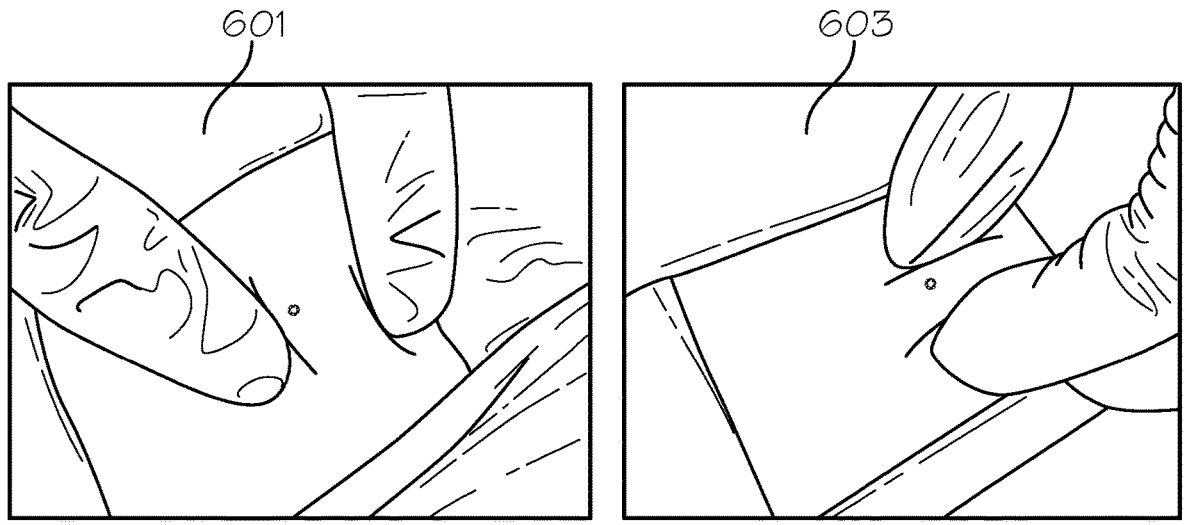
FIGS. 6A to 6D show step by step photographs of the Feel, Find and Follow procedure.

In FIG. 6A, the Feel step is shown. As shown, a user feels the device boundaries using device length (shown in photograph 601) and width (shown in photograph 603).

Figure 6B:
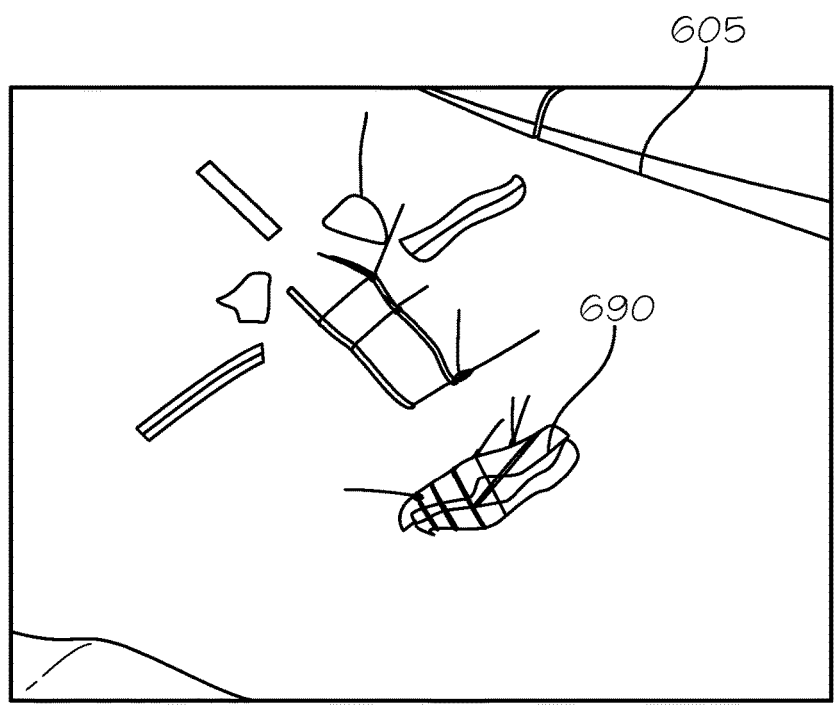

For first time cannulation the needle direction may be determined using incision site 690 as shown in photograph 605 of FIG. 6B. The needle direction may be away from the incision site 690. The needle entry point may be located at approximately at a position a third of the device length from the proximal end, or approximately 15 mm from the incision site.

Figure 6C:
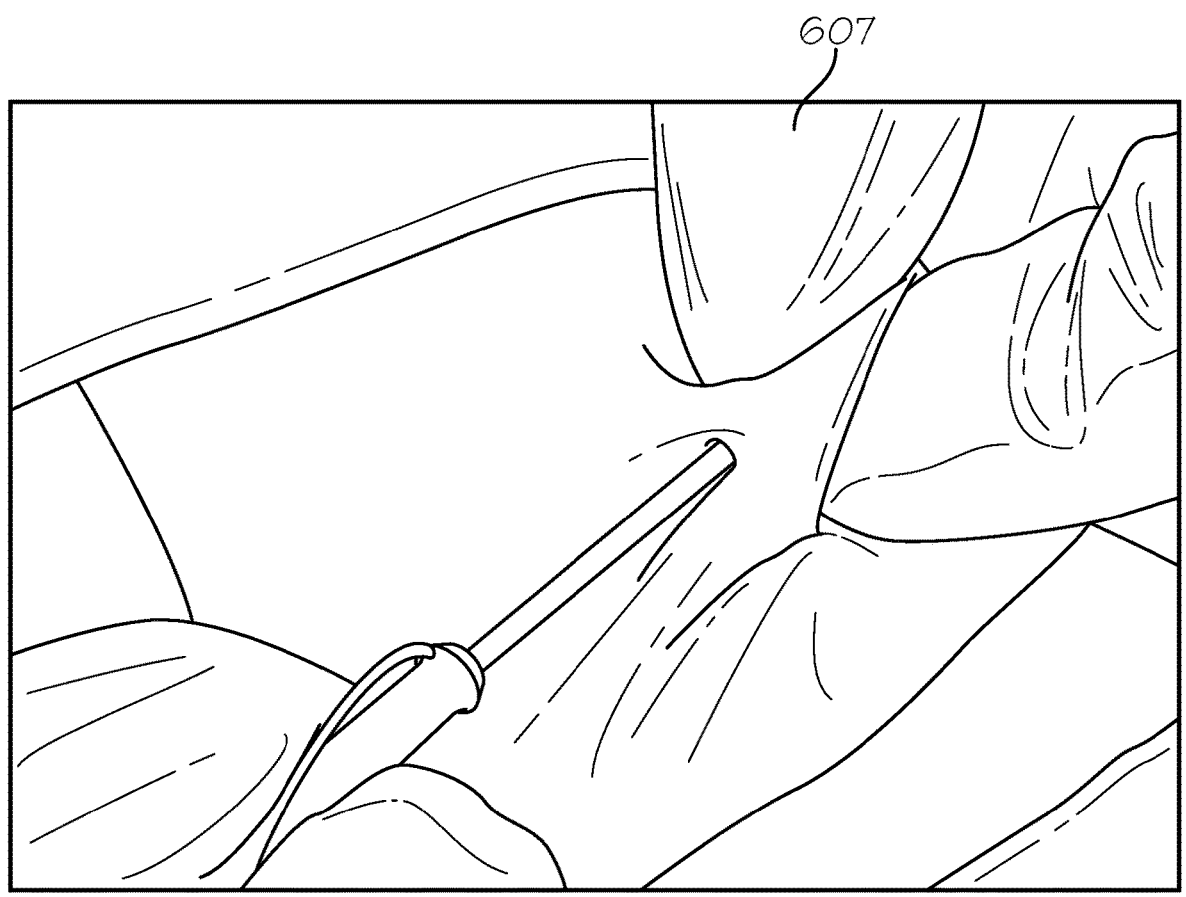

In FIG. 6C, the Find step is shown. In the Find step, the cannulation lumen entry point may be found using the device length to scab location for determining the needle direction as shown in photograph 607. The device may be held in a way whereby one would hold a fistula graft. The needle may then be entered by feeling for the metal device.

Figure 6D:
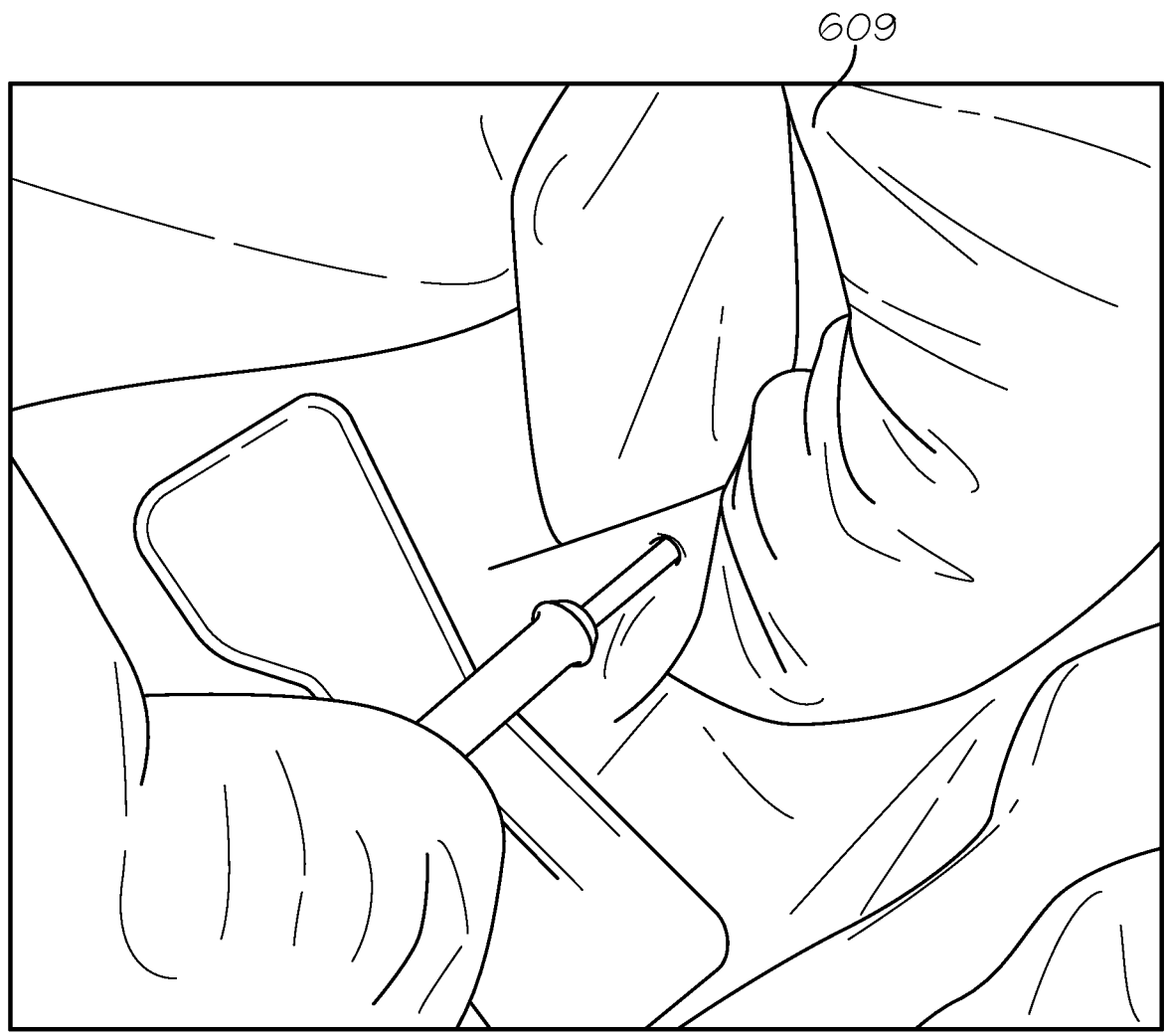

In FIG. 6D, the Follow step is shown. As shown, the needle may be inserted to follow the cannulation lumen to access the fistula as shown in photograph 609. On successful cannulation, there may be flashback. If flashback is not immediately observed, one may fine tune and adjust the needling direction. The device may be configured to withstand "jiggle" movements. If flashback continues to not be observed, one may retract the needle and repeat the above steps.

According to various embodiments, there may be provided a method to perform easy vascular access. For example, a person who has lower skill as compared to the nurse, such as the patient himself may perform the vascular access. The method may be minimally painful and/or painless. The method may be performed by the creation of a high quality buttonhole track while maintaining accurate access via the buttonhole track with the aid of a permanent implant.

According to various embodiments, a method of creating a scarred tissue track for easy and minimally painful vascular access includes implanting a permanent needle guide device under the skin and above the vessel. The method may further include ["Feel it"] feeling for the boundary of the permanent needle guide device embedded under the skin, to know where to needle and in what direction. The method may further include ["Find it"] finding the inner lumen of the permanent needle guide device by pinching the indented part of top surface of said device, said indentation at half to one third from the proximal end of said device. The method may also include piercing a sharp needle through the skin, into the device. The method may further include ["Follow it"] letting the sharp needle follow the angle of the lumen of the permanent needle guide device to access the vessel at an optimal and consistent angle.

According to various embodiments, the method may include repeating the "Feel it", "Find it" and "Follow it" steps every 1-5 days consistently via the same spot on the skin, at an exact same angle as guided by the permanent implant needle guide.

According to various embodiments, the method may include forming a scarred tissue track from under the skin, through the implant needle guide, linking to the vessel.

According to various embodiments, the method may include switching to a blunt needle or non-traumatic vascular access element to gain access to the vessel via the scarred tissue track. For example, like putting on an earring whereby the earring hole with fibrosed tissue has no pain receptors.

According to various embodiments, there is provided a method of maintaining accurate access via a buttonhole track for easy and minimally painful vascular access. The method may include performing the method as described above to create a scarred tissue track for easy and minimally painful vascular access.

According to various embodiments, the method may further include ["Feel it"] feeling for the boundary of the permanent needle guide device embedded under the skin, to know where to needle and in what direction.

According to various embodiments, the method may further include ["Find it"] finding the inner lumen of the permanent needle guide device by pinching an indented part of a top surface of said device, said indentation at half to one third from the proximal end of said device. The method may further include piercing a blunt needle or a non-traumatic vascular access element through the skin, into the device.

According to various embodiments, the method may include ["Follow it"] letting the blunt needle or the non-traumatic vascular access element to follow the angle of the lumen of the permanent needle guide device to access the vessel at an optimal and consistent angle, via an angle that does not hurt the Buttonhole Track.

Figure 7A:
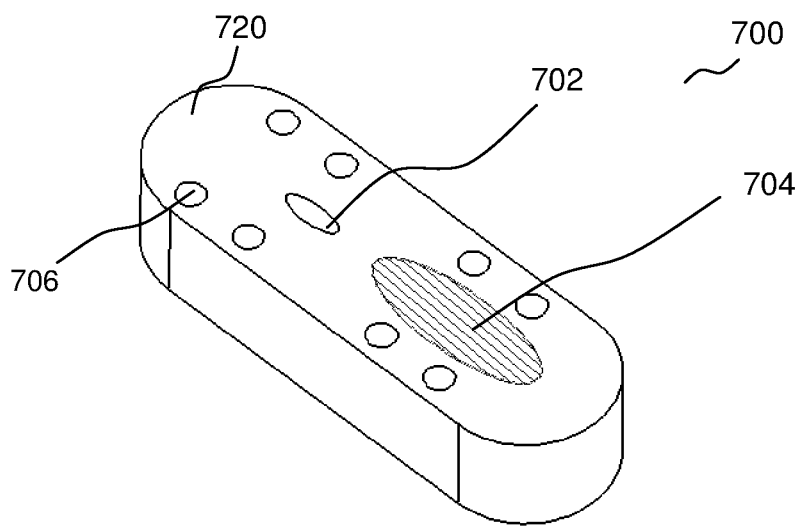
FIGS. 7A to 7C show various embodiments an implantable device according to various embodiments.
Figure 7A:
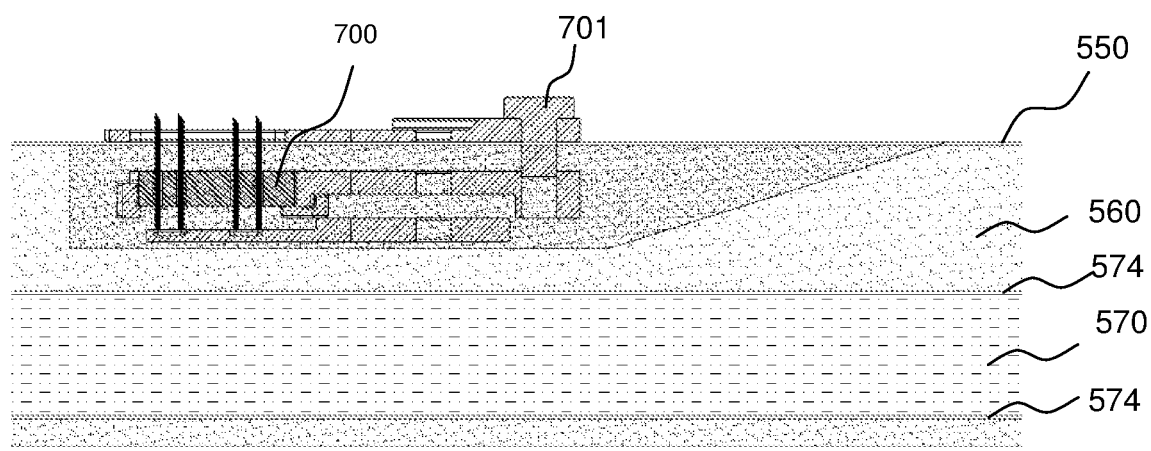
Figure 7B:
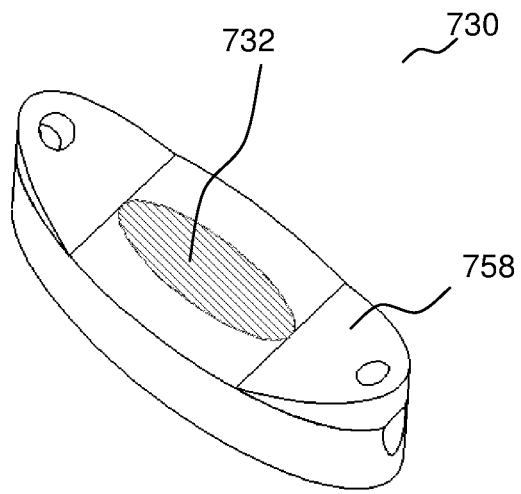
Figure 7C:
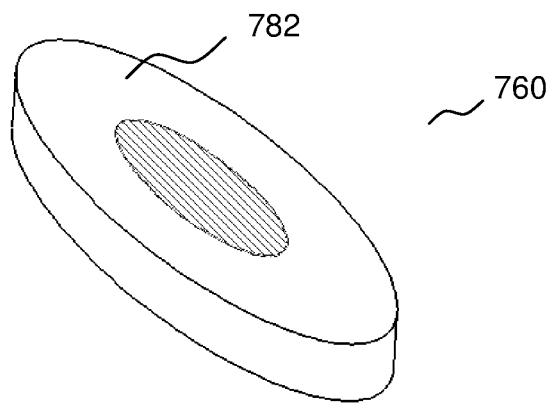

FIGS. 7A to 7C show various embodiments of a vascular access device (in other words an implantable device) 700, 730, 760.

FIG. 7A shows a disc shaped vascular access device 700 including automated suture ports loaded with sutures and needles according to various embodiments. The device 700 may include a flat top profile 720 and an angled dialysis needle access channel 702, with similar advantages as the devices 200, 230 and 260 described in FIGS. 2A-2C. The device 700 may differ from the devices 200, 230 and 260 of FIGS. 2A-2C in that there are eight vertical dermis-anchor ports 706, each configured for containing special straight needles pre-loaded with sutures. The device 700 may further be adapted to be coupled as a system with a subcutaneous delivery device 701, such as one described in a Singapore patent application entitled "Delivery Device For Implantation Of A Subcutaneous Implant" filed on 8 Jan. 2015, said subcutaneous delivery device 701 may be able to automatically deploy suture needles to pierce through the skin to suture the device 700 onto the skin, at the trigger of a needle anvil. Advantageously, the auto suture function will eradicate any possibility of the user mistakenly missing the dermis-anchor ports and the suture not catching the device when sutured onto the skin.

The device 700 may further differ from the devices 200, 230 and 260 of FIGS. 2A-2C in that the device 700 may not contain rounded edges. This may allow a distinct tactile feel to locate the boundaries of the implanted device 700 and the entry point from the skin to cannulation channel. This may provide an additional assurance and confidence for an accurate cannulation.

The device 700 may further differ from the devices 200, 230 and 260 of FIGS. 2A-2C in that, the device 700 may include an orientation channel 704 with a trajectory parallel to the needle access channel 702, for example at 20 degrees (unlike the devices 200, 230 and 260 of FIGS. 2A-2C where the orientation channels 204, 234, 264 for test needles are vertical). The orientation channel 704 of the device 700 may accommodate a maximum of up to 25 G sized test needle. The angled hole 704 may be accessed during implantation and guides the needle to ascertain accurate orientation of the device 700. Orientation is confirmed by a successful flashback obtained upon cannulation of the target vessel.

FIG. 7B shows a disc-shaped vascular access device (in other words an implantable device) 730 with raised corners 758 at both ends of its top surface 750 according to various embodiments. This profile with raised ends 758 may allow a distinct tactile feel to locate boundaries of cannulation, an indication of cannulation safety for the patient. This may also provide an additional assurance and confidence for an accurate cannulation. The two raised corners 758 also act as dermis-anchor ports for sutures to catch and anchor the device onto the dermis.

FIG. 7C shows a disc-shaped vascular access device (in other words an implantable device) 760 with no suture ports, configured to work together with tissue glue. Similar to the devices 200 of FIG. 2A, the device 760 may include an elliptical shape with limited rotational symmetry, to allow user to identify the orientation of the device 760 via tactile feel. The device 760 may not include dermis-anchor ports and may not relay on suturing as the transition anchoring technique to fixate onto the dermis. Instead, the device 760 may be configured to optimize anchoring via adhesive-based mechanisms. The flat surfaces 782 along the height of the device 760 may maximize the surface area for adhesive-based transition anchoring mechanisms, including but not limited to tissue glue, subcutaneous suturing and other means of adhesives and biocompatible fasteners, to be used to anchor the device with the subcutaneous tissue. Accordingly, the anchoring means for device 760 may be in the form of the adhesive-based mechanisms including tissue glue, adhesive means and biocompatible fasteners.

According to the various embodiments, there is provided an apparatus for guiding an access member (for example a dialysis needle) to access a vasculature (for example an AV fistula) via a consistent site and along a consistent angular trajectory in the tissue so as to preserve the health of the vasculature, particularly during the "Wear & Tear" phase in which the access member is required to repeatedly cannulate the vasculature (for example during recurring dialysis treatment). Accordingly, various embodiments may provide an apparatus or a device that guides an access member to access a vasculature via a consistent site and creates a tunneled fibrosed track. The apparatus or the device may be implanted sub-dermis in subcutaneous tissue. The apparatus or the device may be first anchored to the dermis, next anchored to the fibrosed subcutaneous tissue encapsulated around the device. The apparatus or the device may include at least one lumen to guide the vascular access member to access the vessel along a consistent trajectory. The apparatus or the device may not be anchored to the target vessel to allow room for tissue to be present between the apparatus and the target vessel.

According to various embodiments, there may be provided an implantable device or a subcutaneous implantable device for guiding a vascular access member. The device may include a channel defined by a through-hole in the device. The channel may be configured to guide the vascular access member therethrough to a vascular site. The device may include a plurality of anchoring mechanism configured to anchor the device to the dermis and/or the subcutaneous tissue in a fixed position, and away from the vascular site, to allow repeated access through the channel to the vascular site.

According to various embodiments, the device may further include a top surface, an opposing bottom surface and a sidewall extending between the top surface and the opposing bottom surface, wherein the top surface and the opposing bottom surface is less than 6 mm apart to enable the device to be slipped through an incision less than 6 mm deep from the skin.

According to various embodiments, the device may further include a top surface, an opposing bottom surface and a sidewall extending between the top surface and the opposing bottom surface, wherein the top surface and the opposing bottom surface are substantially parallel to each other.

According to various embodiments, the device may further include a top surface, an opposing bottom surface and a sidewall extending between the top surface and the opposing bottom surface, wherein the bottom surface is at least substantially flat.

According to various embodiments, the device may further include a top surface, an opposing bottom surface and a sidewall extending between the top surface and the opposing bottom surface, wherein the top surface has distinct edges that enables orientation of the device to be determined through tactile feel.

According to various embodiments, the channel may include an inlet and an outlet, wherein the inlet may be positioned on the top surface of the device through which the vascular access member enters and the outlet may be positioned on the opposing bottom surface of the device from which the vascular access member exits.

According to various embodiments, a centre axis of the channel may form an acute angle relative to the top surface of the device.

According to various embodiments, the anchoring mechanism may include at least one attachment passage configured to allow at least one attachment member to extend therethrough and/or tissue to in-growth therethrough.

According to various embodiments, the at least one attachment passage may be arranged along the sidewall.

According to various embodiments, the at least one attachment passage may be arranged on the top surface.

Advantageously, embodiments of the device may be implanted subcutaneously and non-invasive to an arteriovenous fistula (AVF). Thus, the device may preserve the lifespan of the AVF and reduces cannulation-associated complications. The device may further minimize cannulation pain, and enable non-medically trained personnel to perform vascular access independently. Embodiments of the device may be a permanent but explantable device. The device may be implanted in a treatment room within a simple 20 min outpatient procedure.

For implantation procedure, advantageously, embodiments of the device may require only a shallow and short slit on the skin to implant the device. The device may "slip" under the skin, instead of through a deep and rounded incision that accesses the target vessel, for example the arteriovenous fistula (AVF). The device may allow implantation to be done outside the operating theatre. The device may not be required to be fixated onto the AVF. Thus, the device may be non-invasive to the AVF.

After the embodiments of the device are implanted and before a scarred down buttonhole track is formed, advantageously, the device may guide a needle to access the AVF without requiring the device to be fixated onto the AVF. The device may also accurately create a buttonhole track leading from the skin to the AVF without requiring the device to be fixated on the AVF. The over-sized ports may allow the device to be anchored on the dermis from beneath the dermis easily. The through-holes may allow tissue in-growth across the device to anchor device to subcutaneous tissue. The buttonhole track created across the central lumen of the device and sticks with the AVF, may act as a complementary anchor to the subcutaneous tissue in a fix relative position to the AVF. The flat top surface with no sharp protruded points may prevent expulsion from skin. The flat bottom surface may prevent erosion into AVF and may facilitate AVF hemostasis post dialysis. The rounded edges may prevent expulsion through the skin, may mitigate pointed edges that could cause injury to AVF, and may facilitate complete subcutaneous tissue encapsulation around the device. The sandblasted surfaces may promote adhesion to subcutaneous tissue as another mechanism to anchor device with subcutaneous tissue. The device may allow faster formation of buttonhole track than manual blind needling method. The device may allow better quality and single tunneled track to be formed than manual blind needling method. The device may require a lower skill requirement to create buttonhole track.

After a scarred-down buttonhole track is formed, in addition to the above advantages, embodiments of the device may further shield erroneous needling from piercing across the buttonhole track from the wrong entry point, thereby avoiding damage to the track. The device may protect from erroneous needling entering from the right entry point but at a wrong angle, thereby avoiding the creation of undesirable side tracks within the buttonhole track. The device may require a lower skill requirement to continually access the AVF via the buttonhole track.

Embodiments of the device may be configured to be held in place by the subcutaneous tissue via the tissue in-growth channels, tissue encapsulation promoted by round edges, sandblasted surfaces that promotes adheres. Subcutaneous tissue anchoring may be further aided after buttonhole track is formed running across the inner lumen of the device. The device may not be attached to the vein. The device in most occasions may further not be touching the vein. The bottom of the device may deliberately be designed to be flat to aid hemostasis. The exit point of the needle lumen may be at the corner of the device to direct the needle to pierce the vein at a position not under the device. This may be to aid hemostasis. When compression is made from the skin, it may be as if there may not be any foreign body above the puncture site, thus no change in current technique to do hemostasis. The device may be flat on the top and fully embedded under the skin. Nothing percutaneous may protrude out of the skin that could promote infection. The device may be elliptical in shape so when the nurse/patient feel for the boundaries of the device, the nurse/patient knows which direction to needle. A buttonhole scarred track may be created from the aid of the device that runs across the device to the vein. Due to consistency enabled by the device, said buttonhole track may be created with 100% predictability, may be of higher quality (no multiple tracks), and may be created within a shorter period of time than manual blind needling (average ~2 wks instead of 20 wks). The device boundaries may be optimally round edged after much animal R&D. This may prevent the device from eroding through the skin. This may also optimize the tissue encapsulation for the subcutaneous tissue to scar around the device and trap it in place. The device may be sandblasted to promote tissue adhesion to anchor the device in place with the subcutaneous tissue. The device may be designed with a thinnest possible disc profile to enable the device to be very easily implanted under the skin, without the need of being in an operating theatre, under local anesthesia, with minimal trauma to the skin or subcutaneous tissue, with no trauma to the target vessel.

Embodiments of the vascular access device as described herein may preserve fistula health, reduce dialysis cost and return quality of life to kidney failure patients. The device may enable easy and less painful access that preserves the health of an AV fistula. The device may be a titanium metal implant placed under the skin just above the AV fistula. Two of the devices may be implanted per patient at the arterial and venous sites.

Embodiments of the device may function to achieve buttonhole creation for creation of high quality, single track buttonhole by any nurse using a sharp needle. The device may also function to achieve buttonhole maintenance for maintaining consistent, accurate buttonhole access by any one using a blunt needle.

Advantageously, the device may yield the following benefits. The device may extend AV fistula life span. The device may reduce cannulation pain. The device may reduce fistula complication. The device may eliminate the need for skilled cannulators to create and maintain buttonhole. The device may promote self-cannulation and support home haemodialysis. The device may reduce missed cannulation, needle infiltration and hematoma development. The device may enable higher success rate of creating buttonhole tracks on fistula with limited area available for cannulation.

While the invention has been particularly shown and described with reference to specific embodiments, it should be understood by those skilled in the art that various changes in form and detail may be made therein without departing from the scope of the invention as defined by the appended claims. The scope of the invention is thus indicated by the appended claims and all changes which come within the meaning and range of equivalency of the claims are therefore intended to be embraced.

The applications of the disclosed invention discussed above are also not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

The invention claimed is:

1. A subcutaneous implantable device for guiding a vascular access member, the device comprising:
   a top surface and an opposing bottom surface, an entirety of the opposing bottom surface parallel to and dimensioned with a thickness of 6 mm or less from an entirety of the top surface from an entirety of the top surface, with a sidewall joining the top surface and the opposing bottom surface and a channel defined by a through-hole extending from the top surface to the opposing bottom surface of the device, wherein the channel is configured to guide the vascular access member therethrough to a vascular site on a blood vessel; and
   an anchor comprising holes arranged at least partially on a portion of the sidewall of the device, the sidewall perpendicular to the top surface and the bottom surface, the holes configured to attach the device via tissue in-growth to at least one of a dermis or a subcutaneous tissue at a position underneath the dermis, wherein the device is dimensioned to allow the device to be attached through the anchor for anchoring the device at a distance away from the vascular site.

2. The device of claim 1, wherein the anchor is further configured to fixedly attach the device to at least one of the dermis or the subcutaneous tissue to allow repeated access of the vascular access member through the channel to the vascular site.

3. The device of claim 1, wherein the anchor is configured to fixedly attach the device to the at least one of the dermis or the subcutaneous tissue for the channel to consistently guide the vascular access member to repeatedly access a same location of the vascular site, via a same angle and via a same location of the dermis.

4. The device of claim 1, wherein the anchor comprises:
at least one subcutaneous anchor configured to attach, in a form of using suture or tissue in-growth or tissue encapsulation or a tissue adhesion, the device to the subcutaneous tissue at the position underneath the dermis of the subcutaneous tissue.

5. The device as claimed in claim 4, wherein the device is configured to exert a compression on a layer of subcutaneous tissue between the device and the vascular site in response to a normal compression applied to the dermis to facilitate hemostasis of the vascular site.

6. The device of claim 4, wherein the anchor further comprises at least one dermis anchor configured to attach the device to the dermis using suture or tissue adhesion.

7. The device of claim 4, wherein the subcutaneous anchor is configured to fixedly attach the device to the subcutaneous tissue adjacent and non-invasive to the vascular site.

8. The device of claim 1 wherein the device is configured to enable the device to be implanted through an incision having a depth of less than 6 mm.

9. The device of claim 8, wherein the opposing bottom surface is flat.

10. The device of claim 8, wherein the top surface comprises corners, raised profiles, or protrusions for enabling an orientation of the device to be determined through tactile feel.

11. The device of claim 8, wherein the top surface and the bottom surface are elliptical, or triangular, or "I"-shaped.

12. The device of claim 8, wherein the sidewall extends from the top surface at an interface which comprises a curved edge, and wherein the sidewall extends from the opposing bottom surface at another interface which comprises a further curved edge.

13. The device of claim 8, wherein the channel comprises an inlet positioned on the top surface of the device through which the vascular access member enters, and an outlet positioned on the opposing bottom surface of the device from which the vascular access member exits.

14. The device of claim 8, wherein a center axis of the channel forms an acute angle of about 5 degrees to about 45 degrees relative to the top surface of the device.

15. The device of claim 14, wherein the channel is configured to guide the vascular access member towards the vascular site outside a footprint of the device.

16. The device of claim 1, wherein the anchor comprises an anchoring passage configured to allow the device to be sutured to at least one of the dermis or the subcutaneous tissue and to allow tissue in-growth therethrough.

17. The device of claim 4, wherein the subcutaneous anchor comprises an anchoring passage configured to allow the device to be sutured to at least one of the dermis or the subcutaneous tissue and to allow tissue in-growth therethrough.

18. The device of claim 1, wherein the thickness of 6 mm or less allows the device to be attached through the anchor for anchoring the device at the distance away from the vascular site.

* * * * *